United States Patent [19]

Morrow

[11] Patent Number: 5,614,413
[45] Date of Patent: Mar. 25, 1997

[54] ENCAPSIDATED RECOMBINANT POLIOVIRUS NUCLEIC ACID AND METHODS OF MAKING AND USING SAME

[75] Inventor: Casey D. Morrow, Birmingham, Ala.

[73] Assignee: The UAB Research Foundation, Birmingham, Ala.

[21] Appl. No.: 589,446

[22] Filed: Jan. 22, 1996

Related U.S. Application Data

[63] Continuation of Ser. No. 87,009, Jul. 1, 1993, abandoned.

[51] Int. Cl.$^6$ .............................. C12P 21/02; C12N 15/43
[52] U.S. Cl. ................... 435/320.1; 435/69.3; 435/172.1
[58] Field of Search .............................. 435/172.1, 320.1, 435/69.3; 424/208.1, 217.1, 199.1

[56] References Cited

PUBLICATIONS

J.L. Fox (1994) Bio /Technology 12:128.
F.D. Ledley (1991) Human Gene Therapy 2:77–83.
A. Knuth et al. (1991) Current Opinion in Immunology 3:659–664.
D. C. Porter et al. (1993) J. Virology 67(7).
Porter D.C. et al. (Mar. 13–18 1993) "Encapsidation of Chimeric HIV-1-Poliovirus Minireplicons" *J. Cell Biochem Suppl.* 17 (D): p. 26.
Ansardi, D.C. et al. (Mar.13–18 1993) "Molecular Analysis of Poliovirus Assembly Using Recombinant Vaccina Viruses to Complement A Poliovirus Genome With A Capsid Gene Deletion" *J. Cell Biochem. Suppl.* 17 (D); p. 22.
Bass, J.W. et al. (1979) "Oral Polio Vaccine: Effect of Booster Vaccination One to 14 Years After Primary Series" JAMA 239(21); 2252–2255.
Ogra, P.L. and Karzon, D.T. (1971) "Formation and Function of Poliovirus Antibody in Different Tissues" *Prog. Med. Virol.* 13:156–193.
Conry, R.M. et al. (1995) *J. Immunol.* (Abstract from the Nov. 1–4, 1995 10th Annual Scientific Meeting of the Society for Biological Therapy, Williamsburg, VA).
Ansardi, D.C. et al. (1994) "Characterization of Poliovirus Replicons Encoding Carcinoembyonic Antigen" *Cancer Research* 54:6359–6364.
Kantor, J. et al. (1992) "Antitumor Activity and Immune Responses Induced by a Recombinant Carcinoembryonic Antigen–Vaccina Virus Vaccine" *J. Natl. Cancer Institute* 84:1084–1091.
Haynes, B.F. (1993) "Scientific and Social Issues of Human Immunodeficiency Virus Vaccine Development" *Science* 260:1279–1286.
Ansardi, D.C. et al. (1992) "Myristylation of Poliovirus Capsid Precursor P1 is Required for Assembly of Subviral Particles" *J. Virol.* 66(7):4556–4563.

McGhee, J.R. and Mestecky, J. (1992) "The Mucosal Immune System in HIV Infection and Prospects for Mucosal Immunity to AIDS" *AIDS Res. Rev.* 2:289–312.
Percy, N. et al. (1992) "A Poliovirus Replicon Containing the Chloramphenicol Acetyltransferase Gene Can Be Used To Study the Replication and Encapsidation of Poliovirus RNA" *J. Virol.* 66(8):5040–5046.
Ansardi, D.C. et al. (1991) "Coinfection with Recombinant Vaccina Viruses Expressing Poliovirus P1 and P3 Proteins Results in Polyprotein Processing and Formation of Empty Capsid Structures" *J. Virol.* 65(4):2088–2092.
Choi, W.S. et al. (1990) "Expression of Human Immunodeficiency Virus Type 1 (HIV–1) gag, pol, and env Proteins from Chimeric HIV–1–Poliovirus Minireplicons" *J. Virol.* 65(6):2875–2883.
Jenkins, O. et al. (1990) "An Antigen Chimera of Poliovirus Induces Antibodies Against Human Papillomavirus Type 16" *J. Virol.* 64(3):1201–1206.
Evans, D.J. et al. (1989) "An Engineered Poliovirus Chimera Elicits Broadly Reactive HIV–1 Neutralizing Antibodies" *Nature* 339:385–388.

*Primary Examiner*—George C. Elliott
*Assistant Examiner*—John S. Brusca
*Attorney, Agent, or Firm*—Jean M. Silveri; Lahive & Cockfield

[57] ABSTRACT

The present invention pertains to a method of encapsidating a recombinant poliovirus nucleic acid to obtain a yield of encapsidated viruses which substantially comprises encapsidated recombinant poliovirus nucleic acid. The method of encapsidating a recombinant poliovirus nucleic acid includes contacting a host cell with a recombinant poliovirus nucleic acid which lacks the nucleotide sequence encoding at least a portion of a protein necessary for encapsidation and an expression vector comprising a nucleic acid which encodes at least a portion of one protein necessary for encapsidation under conditions appropriate for introduction of the recombinant poliovirus nucleic acid and the expression vector into the host cell and obtaining a yield of encapsidated viruses which substantially comprises an encapsidated recombinant poliovirus nucleic acid. A foreign nucleotide sequence is generally substituted for the nucleotide sequence of the poliovirus nucleic acid encoding at least a portion of a protein necessary for encapsidation. The invention further pertains to encapsidated recombinant poliovirus nucleic acids produced by the method of this invention and compositions containing the encapsidated recombinant poliovirus nucleic acid containing a foreign nucleotide sequence for use in a method of stimulating an immune response in a subject to the protein encoded by the foreign nucleotide sequence.

64 Claims, 11 Drawing Sheets

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

TATTAGTAGA TCTG 14

( 2 ) INFORMATION FOR SEQ ID NO:2:

( i ) SEQUENCE CHARACTERISTICS:

(A) LENGTH: 14 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:2:

TACAGATGTA CTAA 14

(2) INFORMATION FOR SEQ ID NO:3:

(i) SEQUENCE CHARACTERISTICS:
(A) LENGTH: 845 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 20..845

(xi) SEQUENCE DESCRIPTION: SEQ ID NO:3:

```
ACACAGCAAT CAGGTCAGC CAA AAT TAC CCT ATA GTG CAG AAC ATC CAG GGG      52
                    Gln Asn Tyr Pro Ile Val Gln Asn Ile Gln Gly
                     1               5                  10

CAA ATG GTA CAT CAG GCC ATA TCA CCT AGA ACT TTA AAT GCA TGG GTA      100
Gln Met Val His Gln Ala Ile Ser Pro Arg Thr Leu Asn Ala Trp Val
             15                  20                  25

AAA GTA GTA GAA GAG AAG GCT TTC AGC CCA GAA GTG ATA CCC ATG TTT      148
Lys Val Val Glu Glu Lys Ala Phe Ser Pro Glu Val Ile Pro Met Phe
         30                  35                  40

TCA GCA TTA TCA GAA GGA GCC ACC CCA CAA GAT TTA AAC ACC ATG CTA      196
Ser Ala Leu Ser Glu Gly Ala Thr Pro Gln Asp Leu Asn Thr Met Leu
     45                  50                  55

AAC ACA GTG GGG GGA CAT CAA GCA GCC ATG CAA ATG TTA AAA GAG ACC      244
Asn Thr Val Gly Gly His Gln Ala Ala Met Gln Met Leu Lys Glu Thr
 60                  65                  70                  75

ATC AAT GAG GAA GCT GCA GAA TGG GAT AGA GTG CAT CCA GTG CAT GCA      292
Ile Asn Glu Glu Ala Ala Glu Trp Asp Arg Val His Pro Val His Ala
                 80                  85                  90

GGG CCT ATT GCA CCA GGC CAG ATG AGA GAA CCA AGG GGA AGT GAC ATA      340
Gly Pro Ile Ala Pro Gly Gln Met Arg Glu Pro Arg Gly Ser Asp Ile
             95                 100                 105

GCA GGA ACT ACT AGT ACC CTT CAG GAA CAA ATA GGA TGG ATG ACA AAT      388
Ala Gly Thr Thr Ser Thr Leu Gln Glu Gln Ile Gly Trp Met Thr Asn
         110                 115                 120

AAT CCA CCT ATC CCA GTA GGA GAA ATT TAT AAA AGA TGG ATA ATC CTG      436
Asn Pro Pro Ile Pro Val Gly Glu Ile Tyr Lys Arg Trp Ile Ile Leu
    125                 130                 135

GGA TTA AAT AAA ATA GTA AGA ATG TAT AGC CCT ACC AGC ATT CTG GAC      484
Gly Leu Asn Lys Ile Val Arg Met Tyr Ser Pro Thr Ser Ile Leu Asp
140                 145                 150                 155

ATA AGA CAA GGA CCA AAG GAA CCC TTT AGA GAC TAT GTA GAC CGG TTC      532
Ile Arg Gln Gly Pro Lys Glu Pro Phe Arg Asp Tyr Val Asp Arg Phe
                160                 165                 170

TAT AAA ACT CTA AGA GCC GAG CAA GCT TCA CAG GAG GTA AAA AAT TGG      580
Tyr Lys Thr Leu Arg Ala Glu Gln Ala Ser Gln Glu Val Lys Asn Trp
            175                 180                 185

ATG ACA GAA ACC TTG TTG GTC CAA AAT GCG AAC CCA GAT TGT AAG ACT      628
Met Thr Glu Thr Leu Leu Val Gln Asn Ala Asn Pro Asp Cys Lys Thr
        190                 195                 200
```

| | | | | | | | | | | | | | | | | |
|---|---|---|---|---|---|---|---|---|---|---|---|---|---|---|---|---|
| ATT | TTA | AAA | GCA | TTG | GGA | CCA | GCG | GCT | ACA | CTA | GAA | GAA | ATG | ATG | ACA | 676 |
| Ile | Leu | Lys | Ala | Leu | Gly | Pro | Ala | Ala | Thr | Leu | Glu | Glu | Met | Met | Thr | |
| | 205 | | | | 210 | | | | | 215 | | | | | | |
| GCA | TGT | CAG | GGA | GTA | GGA | GGA | CCC | GGC | CAT | AAG | GCA | AGA | GTT | TTG | GCT | 724 |
| Ala | Cys | Gln | Gly | Val | Gly | Gly | Pro | Gly | His | Lys | Ala | Arg | Val | Leu | Ala | |
| 220 | | | | 225 | | | | | 230 | | | | | | 235 | |
| GAA | GCA | ATG | AGC | CAA | GTA | ACA | AAT | TCA | GCT | ACC | ATA | ATG | ATG | CAG | AGA | 772 |
| Glu | Ala | Met | Ser | Gln | Val | Thr | Asn | Ser | Ala | Thr | Ile | Met | Met | Gln | Arg | |
| | | | | 240 | | | | | 245 | | | | | 250 | | |
| GGC | AAT | TTT | AGG | AAC | CAA | AGA | AAG | ATT | GTT | AAG | TGT | TTC | AAT | TGT | GGC | 820 |
| Gly | Asn | Phe | Arg | Asn | Gln | Arg | Lys | Ile | Val | Lys | Cys | Phe | Asn | Cys | Gly | |
| | | | 255 | | | | | 260 | | | | | 265 | | | |
| AAA | GAA | GGG | CAC | ACA | GCC | AGA | AAG | T | | | | | | | | 845 |
| Lys | Glu | Gly | His | Thr | Ala | Arg | Lys | | | | | | | | | |
| | | 270 | | | | | 275 | | | | | | | | | |

( 2 ) INFORMATION FOR SEQ ID NO:4:

( i ) SEQUENCE CHARACTERISTICS:
        ( A ) LENGTH: 275 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Gln | Asn | Tyr | Pro | Ile | Val | Gln | Asn | Ile | Gln | Gly | Gln | Met | Val | His | Gln |
| 1 | | | | 5 | | | | | 10 | | | | | 15 | |
| Ala | Ile | Ser | Pro | Arg | Thr | Leu | Asn | Ala | Trp | Val | Lys | Val | Val | Glu | Glu |
| | | | 20 | | | | | 25 | | | | | 30 | | |
| Lys | Ala | Phe | Ser | Pro | Glu | Val | Ile | Pro | Met | Phe | Ser | Ala | Leu | Ser | Glu |
| | | 35 | | | | | 40 | | | | | 45 | | | |
| Gly | Ala | Thr | Pro | Gln | Asp | Leu | Asn | Thr | Met | Leu | Asn | Thr | Val | Gly | Gly |
| | 50 | | | | | 55 | | | | | 60 | | | | |
| His | Gln | Ala | Ala | Met | Gln | Met | Leu | Lys | Glu | Thr | Ile | Asn | Glu | Glu | Ala |
| 65 | | | | | 70 | | | | | 75 | | | | | 80 |
| Ala | Glu | Trp | Asp | Arg | Val | His | Pro | Val | His | Ala | Gly | Pro | Ile | Ala | Pro |
| | | | | 85 | | | | | 90 | | | | | 95 | |
| Gly | Gln | Met | Arg | Glu | Pro | Arg | Gly | Ser | Asp | Ile | Ala | Gly | Thr | Thr | Ser |
| | | | 100 | | | | | 105 | | | | | 110 | | |
| Thr | Leu | Gln | Glu | Gln | Ile | Gly | Trp | Met | Thr | Asn | Asn | Pro | Pro | Ile | Pro |
| | | 115 | | | | | 120 | | | | | 125 | | | |
| Val | Gly | Glu | Ile | Tyr | Lys | Arg | Trp | Ile | Ile | Leu | Gly | Leu | Asn | Lys | Ile |
| | 130 | | | | | 135 | | | | | 140 | | | | |
| Val | Arg | Met | Tyr | Ser | Pro | Thr | Ser | Ile | Leu | Asp | Ile | Arg | Gln | Gly | Pro |
| 145 | | | | | 150 | | | | | 155 | | | | | 160 |
| Lys | Glu | Pro | Phe | Arg | Asp | Tyr | Val | Asp | Arg | Phe | Tyr | Lys | Thr | Leu | Arg |
| | | | | 165 | | | | | 170 | | | | | 175 | |
| Ala | Glu | Gln | Ala | Ser | Gln | Glu | Val | Lys | Asn | Trp | Met | Thr | Glu | Thr | Leu |
| | | | 180 | | | | | 185 | | | | | 190 | | |
| Leu | Val | Gln | Asn | Ala | Asn | Pro | Asp | Cys | Lys | Thr | Ile | Leu | Lys | Ala | Leu |
| | | 195 | | | | | 200 | | | | | 205 | | | |
| Gly | Pro | Ala | Ala | Thr | Leu | Glu | Glu | Met | Met | Thr | Ala | Cys | Gln | Gly | Val |
| | 210 | | | | | 215 | | | | | 220 | | | | |
| Gly | Gly | Pro | Gly | His | Lys | Ala | Arg | Val | Leu | Ala | Glu | Ala | Met | Ser | Gln |
| 225 | | | | | 230 | | | | | 235 | | | | | 240 |
| Val | Thr | Asn | Ser | Ala | Thr | Ile | Met | Met | Gln | Arg | Gly | Asn | Phe | Arg | Asn |
| | | | | 245 | | | | | 250 | | | | | 255 | |

(2) INFORMATION FOR SEQ ID NO:5:

(i) SEQUENCE CHARACTERISTICS:
        (A) LENGTH: 948 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 4..946

(xi) SEQUENCE DESCRIPTION: SEQ ID NO:5:

```
Gln Arg Lys Ile Val Lys Cys Phe Asn Cys Gly Lys Glu Gly His Thr
            260                 265                 270
Ala Arg Lys
        275

AAC CAA TGG CCA TTG ACA GAA GAA AAA ATA AAA GCA TTA GTA GAA ATT      48
    Gln Trp Pro Leu Thr Glu Glu Lys Ile Lys Ala Leu Val Glu Ile
     1               5                  10                  15

TGT ACA GAG ATG GAA AAG GAA GGG AAA ATT TCA AAA ATT GGG CCT GAA      96
Cys Thr Glu Met Glu Lys Glu Gly Lys Ile Ser Lys Ile Gly Pro Glu
                 20                  25                  30

AAT CCA TAC AAT ACT CCA GTA TTT GCC ATA AAG AAA AAA GAC AGT ACT     144
Asn Pro Tyr Asn Thr Pro Val Phe Ala Ile Lys Lys Lys Asp Ser Thr
                 35                  40                  45

AAA TGG AGA AAA TTA GTA GAT TTC AGA GAA CTT AAT AAG AGA ACT CAA     192
Lys Trp Arg Lys Leu Val Asp Phe Arg Glu Leu Asn Lys Arg Thr Gln
             50                  55                  60

GAC TTC TGG GAA GTT CAA TTA GGA ATA CCA CAT CCC GCA GGG TTA AAA     240
Asp Phe Trp Glu Val Gln Leu Gly Ile Pro His Pro Ala Gly Leu Lys
 65                  70                  75

AAG AAA AAA TCA GTA ACA GTA CTG GAT GTG GGT GAT GCA TAT TTT TCA     288
Lys Lys Lys Ser Val Thr Val Leu Asp Val Gly Asp Ala Tyr Phe Ser
 80                  85                  90                  95

GTT CCC TTA GAT GAA GAC TTC AGG AAG TAT ACT GCA TTT ACC ATA CCT     336
Val Pro Leu Asp Glu Asp Phe Arg Lys Tyr Thr Ala Phe Thr Ile Pro
                100                 105                 110

AGT ATA AAC AAT GAG ACA CCA GGG ATT AGA TAT CAG TAC AAT GTG CTT     384
Ser Ile Asn Asn Glu Thr Pro Gly Ile Arg Tyr Gln Tyr Asn Val Leu
            115                 120                 125

CCA CAG GGA TGG AAA GGA TCA CCA GCA ATA TTC CAA AGT AGC ATG ACA     432
Pro Gln Gly Trp Lys Gly Ser Pro Ala Ile Phe Gln Ser Ser Met Thr
        130                 135                 140

AAA ATC TTA GAG CCT TTT AGA AAA CAA AAT CCA GAC ATA GTT ATC TAT     480
Lys Ile Leu Glu Pro Phe Arg Lys Gln Asn Pro Asp Ile Val Ile Tyr
145                 150                 155

CAA TAC ATG GAT GAT TTG TAT GTA GGA TCT GAC TTA GAA ATA GGG CAG     528
Gln Tyr Met Asp Asp Leu Tyr Val Gly Ser Asp Leu Glu Ile Gly Gln
160                 165                 170                 175

CAT AGA ACA AAA ATA GAG GAG CTG AGA CAA CAT CTG TTG AGG TGG GGA     576
His Arg Thr Lys Ile Glu Glu Leu Arg Gln His Leu Leu Arg Trp Gly
                180                 185                 190

CTT ACC ACA CCA GAC AAA AAA CAT CAG AAA GAA CCT CCA TTC CTT TGG     624
Leu Thr Thr Pro Asp Lys Lys His Gln Lys Glu Pro Pro Phe Leu Trp
            195                 200                 205

ATG GGT TAT GAA CTC CAT CCT GAT AAA TGG ACA GTA CAG CCT ATA GTG     672
Met Gly Tyr Glu Leu His Pro Asp Lys Trp Thr Val Gln Pro Ile Val
        210                 215                 220

CTG CCA GAA AAA GAC AGC TGG ACT GTC AAT GAC ATA CAG AAG TTA GTG     720
```

|      |      |      |      |      |      |      |      |      |      |      |      |      |      |      |      |     |
|------|------|------|------|------|------|------|------|------|------|------|------|------|------|------|------|-----|
| Leu  | Pro  | Glu  | Lys  | Asp  | Ser  | Trp  | Thr  | Val  | Asn  | Asp  | Ile  | Gln  | Lys  | Leu  | Val  |     |
|      | 225  |      |      |      |      | 230  |      |      |      |      | 235  |      |      |      |      |     |
| GGG  | AAA  | TTG  | AAT  | TGG  | GCA  | AGT  | CAG  | ATT  | TAC  | CCA  | GGG  | ATT  | AAA  | GTA  | AGG  | 768 |
| Gly  | Lys  | Leu  | Asn  | Trp  | Ala  | Ser  | Gln  | Ile  | Tyr  | Pro  | Gly  | Ile  | Lys  | Val  | Arg  |     |
| 240  |      |      |      |      | 245  |      |      |      |      | 250  |      |      |      |      | 255  |     |
| CAA  | TTA  | TGT  | AAA  | CTC  | CTT  | AGA  | GGA  | ACC  | AAA  | GCA  | CTA  | ACA  | GAA  | GTA  | ATA  | 816 |
| Gln  | Leu  | Cys  | Lys  | Leu  | Leu  | Arg  | Gly  | Thr  | Lys  | Ala  | Leu  | Thr  | Glu  | Val  | Ile  |     |
|      |      |      |      | 260  |      |      |      |      | 265  |      |      |      |      | 270  |      |     |
| CCA  | CTA  | ACA  | GAA  | GAA  | GCA  | GAG  | CTA  | GAA  | CTG  | GCA  | GAA  | AAC  | AGA  | GAG  | ATT  | 864 |
| Pro  | Leu  | Thr  | Glu  | Glu  | Ala  | Glu  | Leu  | Glu  | Leu  | Ala  | Glu  | Asn  | Arg  | Glu  | Ile  |     |
|      |      |      | 275  |      |      |      |      | 280  |      |      |      |      | 285  |      |      |     |
| CTA  | AAA  | GAA  | CCA  | GTA  | CAT  | GGA  | GTG  | TAT  | TAT  | GAC  | CCA  | TCA  | AAA  | GAC  | TTA  | 912 |
| Leu  | Lys  | Glu  | Pro  | Val  | His  | Gly  | Val  | Tyr  | Tyr  | Asp  | Pro  | Ser  | Lys  | Asp  | Leu  |     |
|      |      | 290  |      |      |      |      | 295  |      |      |      |      | 300  |      |      |      |     |
| ATA  | GCA  | GAA  | ATA  | CAG  | AAG  | CAG  | GGG  | CAA  | GGC  | CTCGAG |    |      |      |      |      | 948 |
| Ile  | Ala  | Glu  | Ile  | Gln  | Lys  | Gln  | Gly  | Gln  | Gly  |      |      |      |      |      |      |     |
|      |      | 305  |      |      |      | 310  |      |      |      |      |      |      |      |      |      |     |

( 2 ) INFORMATION FOR SEQ ID NO:6:

( i ) SEQUENCE CHARACTERISTICS:
        ( A ) LENGTH: 314 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Gln | Trp | Pro | Leu | Thr | Glu | Glu | Lys | Ile | Lys | Ala | Leu | Val | Glu | Ile | Cys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Thr | Glu | Met | Glu | Lys | Glu | Gly | Lys | Ile | Ser | Lys | Ile | Gly | Pro | Glu | Asn |
|     |     |     | 20  |     |     |     |     | 25  |     |     |     |     | 30  |     |     |
| Pro | Tyr | Asn | Thr | Pro | Val | Phe | Ala | Ile | Lys | Lys | Lys | Asp | Ser | Thr | Lys |
|     |     | 35  |     |     |     |     | 40  |     |     |     |     | 45  |     |     |     |
| Trp | Arg | Lys | Leu | Val | Asp | Phe | Arg | Glu | Leu | Asn | Lys | Arg | Thr | Gln | Asp |
|     | 50  |     |     |     |     | 55  |     |     |     |     | 60  |     |     |     |     |
| Phe | Trp | Glu | Val | Gln | Leu | Gly | Ile | Pro | His | Pro | Ala | Gly | Leu | Lys | Lys |
| 65  |     |     |     |     | 70  |     |     |     |     | 75  |     |     |     |     | 80  |
| Lys | Lys | Ser | Val | Thr | Val | Leu | Asp | Val | Gly | Asp | Ala | Tyr | Phe | Ser | Val |
|     |     |     |     | 85  |     |     |     |     | 90  |     |     |     |     | 95  |     |
| Pro | Leu | Asp | Glu | Asp | Phe | Arg | Lys | Tyr | Thr | Ala | Phe | Thr | Ile | Pro | Ser |
|     |     |     | 100 |     |     |     |     | 105 |     |     |     |     | 110 |     |     |
| Ile | Asn | Asn | Glu | Thr | Pro | Gly | Ile | Arg | Tyr | Gln | Tyr | Asn | Val | Leu | Pro |
|     |     | 115 |     |     |     |     | 120 |     |     |     |     | 125 |     |     |     |
| Gln | Gly | Trp | Lys | Gly | Ser | Pro | Ala | Ile | Phe | Gln | Ser | Ser | Met | Thr | Lys |
|     | 130 |     |     |     |     | 135 |     |     |     |     | 140 |     |     |     |     |
| Ile | Leu | Glu | Pro | Phe | Arg | Lys | Gln | Asn | Pro | Asp | Ile | Val | Ile | Tyr | Gln |
| 145 |     |     |     |     | 150 |     |     |     |     | 155 |     |     |     |     | 160 |
| Tyr | Met | Asp | Asp | Leu | Tyr | Val | Gly | Ser | Asp | Leu | Glu | Ile | Gly | Gln | His |
|     |     |     |     | 165 |     |     |     |     | 170 |     |     |     |     | 175 |     |
| Arg | Thr | Lys | Ile | Glu | Glu | Leu | Arg | Gln | His | Leu | Leu | Arg | Trp | Gly | Leu |
|     |     |     | 180 |     |     |     |     | 185 |     |     |     |     | 190 |     |     |
| Thr | Thr | Pro | Asp | Lys | Lys | His | Gln | Lys | Glu | Pro | Pro | Phe | Leu | Trp | Met |
|     |     | 195 |     |     |     |     | 200 |     |     |     |     | 205 |     |     |     |
| Gly | Tyr | Glu | Leu | His | Pro | Asp | Lys | Trp | Thr | Val | Gln | Pro | Ile | Val | Leu |
|     | 210 |     |     |     |     | 215 |     |     |     |     | 220 |     |     |     |     |
| Pro | Glu | Lys | Asp | Ser | Trp | Thr | Val | Asn | Asp | Ile | Gln | Lys | Leu | Val | Gly |
| 225 |     |     |     |     | 230 |     |     |     |     | 235 |     |     |     |     | 240 |

| | | | | | | | | | | | | | | |
|---|---|---|---|---|---|---|---|---|---|---|---|---|---|---|
| Lys | Leu | Asn | Trp | Ala | Ser | Gln | Ile | Tyr | Pro | Gly | Ile | Lys | Val | Arg | Gln |
| | | | | 245 | | | | 250 | | | | 255 | | |

| Leu | Cys | Lys | Leu | Leu | Arg | Gly | Thr | Lys | Ala | Leu | Thr | Glu | Val | Ile | Pro |
|---|---|---|---|---|---|---|---|---|---|---|---|---|---|---|---|
| | | | 260 | | | | 265 | | | | | 270 | | | |

| Leu | Thr | Glu | Glu | Ala | Glu | Leu | Glu | Leu | Ala | Glu | Asn | Arg | Glu | Ile | Leu |
|---|---|---|---|---|---|---|---|---|---|---|---|---|---|---|---|
| | | 275 | | | | | 280 | | | | | 285 | | | |

| Lys | Glu | Pro | Val | His | Gly | Val | Tyr | Tyr | Asp | Pro | Ser | Lys | Asp | Leu | Ile |
|---|---|---|---|---|---|---|---|---|---|---|---|---|---|---|---|
| | 290 | | | | | 295 | | | | | | 300 | | | |

| Ala | Glu | Ile | Gln | Lys | Gln | Gly | Gln | Gly | Leu |
|---|---|---|---|---|---|---|---|---|---|
| 305 | | | | | 310 | | | | |

( 2 ) INFORMATION FOR SEQ ID NO:7:

( i ) SEQUENCE CHARACTERISTICS:
        ( A ) LENGTH: 1568 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 7..1565

( x i ) SEQUENCE DESCRIPTION: SEQ ID NO:7:

| | | | | | | | | | | | | | | | | |
|---|---|---|---|---|---|---|---|---|---|---|---|---|---|---|---|---|
| GGGGCC | TGT | CCA | AAG | GTA | TCC | TTT | GAG | CCA | ATT | CCC | ATA | CAT | TAT | TGT | | 48 |
| | Cys | Pro | Lys | Val | Ser | Phe | Glu | Pro | Ile | Pro | Ile | His | Tyr | Cys | | |
| | 1 | | | | 5 | | | | | 10 | | | | | | |

| GCC | CCG | GCT | GGT | TTT | GCG | ATT | CTA | AAA | TGT | AAT | AAT | AAG | ACG | TTC | AAT | 96 |
|---|---|---|---|---|---|---|---|---|---|---|---|---|---|---|---|---|
| Ala | Pro | Ala | Gly | Phe | Ala | Ile | Leu | Lys | Cys | Asn | Asn | Lys | Thr | Phe | Asn | |
| 15 | | | | | 20 | | | | | 25 | | | | | 30 | |

| GGA | ACA | GGA | CCA | TGT | ACA | AAT | GTC | AGC | ACA | GTA | CAA | TGT | ACA | CAT | GGA | 144 |
|---|---|---|---|---|---|---|---|---|---|---|---|---|---|---|---|---|
| Gly | Thr | Gly | Pro | Cys | Thr | Asn | Val | Ser | Thr | Val | Gln | Cys | Thr | His | Gly | |
| | | | | 35 | | | | | 40 | | | | | 45 | | |

| ATT | AGG | CCA | GTA | GTA | TCA | ACT | CAA | CTG | CTG | TTA | AAT | GGC | AGT | CTA | GCA | 192 |
|---|---|---|---|---|---|---|---|---|---|---|---|---|---|---|---|---|
| Ile | Arg | Pro | Val | Val | Ser | Thr | Gln | Leu | Leu | Leu | Asn | Gly | Ser | Leu | Ala | |
| | | | 50 | | | | | 55 | | | | | 60 | | | |

| GAA | GAA | GAG | GTA | GTA | ATT | AGA | TCT | GTC | AAT | TTC | ACG | GAC | AAT | GCT | AAA | 240 |
|---|---|---|---|---|---|---|---|---|---|---|---|---|---|---|---|---|
| Glu | Glu | Glu | Val | Val | Ile | Arg | Ser | Val | Asn | Phe | Thr | Asp | Asn | Ala | Lys | |
| | | 65 | | | | | 70 | | | | | 75 | | | | |

| ACC | ATA | ATA | GTA | CAG | CTG | AAC | ACA | TCT | GTA | GAA | ATT | AAT | TGT | ACA | AGA | 288 |
|---|---|---|---|---|---|---|---|---|---|---|---|---|---|---|---|---|
| Thr | Ile | Ile | Val | Gln | Leu | Asn | Thr | Ser | Val | Glu | Ile | Asn | Cys | Thr | Arg | |
| | 80 | | | | | 85 | | | | | 90 | | | | | |

| CCC | AAC | AAC | AAT | ACA | AGA | AAA | AGA | ATC | CGT | ATC | CAG | AGA | GGA | CCA | GGG | 336 |
|---|---|---|---|---|---|---|---|---|---|---|---|---|---|---|---|---|
| Pro | Asn | Asn | Asn | Thr | Arg | Lys | Arg | Ile | Arg | Ile | Gln | Arg | Gly | Pro | Gly | |
| 95 | | | | | 100 | | | | | 105 | | | | | 110 | |

| AGA | GCA | TTT | GTT | ACA | ATA | GGA | AAA | ATA | GGA | AAT | ATG | AGA | CAA | GCA | CAT | 384 |
|---|---|---|---|---|---|---|---|---|---|---|---|---|---|---|---|---|
| Arg | Ala | Phe | Val | Thr | Ile | Gly | Lys | Ile | Gly | Asn | Met | Arg | Gln | Ala | His | |
| | | | | 115 | | | | | 120 | | | | | 125 | | |

| TGT | AAC | ATT | AGT | AGA | GCA | AAA | TGG | AAT | AAC | ACT | TTA | AAA | CAG | ATA | GAT | 432 |
|---|---|---|---|---|---|---|---|---|---|---|---|---|---|---|---|---|
| Cys | Asn | Ile | Ser | Arg | Ala | Lys | Trp | Asn | Asn | Thr | Leu | Lys | Gln | Ile | Asp | |
| | | | 130 | | | | | 135 | | | | | 140 | | | |

| AGC | AAA | TTA | AGA | GAA | CAA | TTC | GGA | AAT | AAT | AAA | ACA | ATA | ATC | TTT | AAG | 480 |
|---|---|---|---|---|---|---|---|---|---|---|---|---|---|---|---|---|
| Ser | Lys | Leu | Arg | Glu | Gln | Phe | Gly | Asn | Asn | Lys | Thr | Ile | Ile | Phe | Lys | |
| | | 145 | | | | | 150 | | | | | 155 | | | | |

| CAA | TCC | TCA | GGA | GGG | GAC | CCA | GAA | ATT | GTA | ACG | CAC | AGT | TTT | AAT | TGT | 528 |
|---|---|---|---|---|---|---|---|---|---|---|---|---|---|---|---|---|
| Gln | Ser | Ser | Gly | Gly | Asp | Pro | Glu | Ile | Val | Thr | His | Ser | Phe | Asn | Cys | |
| | 160 | | | | | 165 | | | | | 170 | | | | | |

| GGA | GGG | GAA | TTT | TTC | TAC | TGT | AAT | TCA | ACA | CAA | CTG | TTT | AAT | AGT | ACT | 576 |
|---|---|---|---|---|---|---|---|---|---|---|---|---|---|---|---|---|
| Gly | Gly | Glu | Phe | Phe | Tyr | Cys | Asn | Ser | Thr | Gln | Leu | Phe | Asn | Ser | Thr | |
| 175 | | | | | 180 | | | | | 185 | | | | | 190 | |

| | | | | | | | | | | | | | | | | |
|---|---|---|---|---|---|---|---|---|---|---|---|---|---|---|---|---|
| TGG | TTT | AAT | AGT | ACT | TGG | AGT | ACT | GAA | GGG | TCA | AAT | AAC | ACT | GAA | GGA | 624 |
| Trp | Phe | Asn | Ser | Thr | Trp | Ser | Thr | Glu | Gly | Ser | Asn | Asn | Thr | Glu | Gly | |
| | | | | 195 | | | | 200 | | | | | 205 | | | |
| AGT | GAC | ACA | ATC | ACC | CTC | CCA | TGC | AGA | ATA | AAA | CAA | ATT | ATA | AAC | ATG | 672 |
| Ser | Asp | Thr | Ile | Thr | Leu | Pro | Cys | Arg | Ile | Lys | Gln | Ile | Ile | Asn | Met | |
| | | | 210 | | | | | 215 | | | | | 220 | | | |
| TGG | CAG | AAA | GTA | GGA | AAA | GCA | ATG | TAT | GCC | CCT | CCC | ATC | AGT | GGA | CAA | 720 |
| Trp | Gln | Lys | Val | Gly | Lys | Ala | Met | Tyr | Ala | Pro | Pro | Ile | Ser | Gly | Gln | |
| | | 225 | | | | | 230 | | | | | 235 | | | | |
| ATT | AGA | TGT | TCA | TCA | AAT | ATT | ACA | GGG | CTG | CTA | TTA | ACA | AGA | GAT | GGT | 768 |
| Ile | Arg | Cys | Ser | Ser | Asn | Ile | Thr | Gly | Leu | Leu | Leu | Thr | Arg | Asp | Gly | |
| | 240 | | | | | 245 | | | | | 250 | | | | | |
| GGT | AAT | AGC | AAC | AAT | GAG | TCC | GAG | ATC | TTC | AGA | CTT | GGA | GGA | GGA | GAT | 816 |
| Gly | Asn | Ser | Asn | Asn | Glu | Ser | Glu | Ile | Phe | Arg | Leu | Gly | Gly | Gly | Asp | |
| 255 | | | | | 260 | | | | | 265 | | | | | 270 | |
| ATG | AGG | GAC | AAT | TGG | AGA | AGT | GAA | TTA | TAT | AAA | TAT | AAA | GTA | GTA | AAA | 864 |
| Met | Arg | Asp | Asn | Trp | Arg | Ser | Glu | Leu | Tyr | Lys | Tyr | Lys | Val | Val | Lys | |
| | | | | 275 | | | | 280 | | | | | 285 | | | |
| ATT | GAA | CCA | TTA | GGA | GTA | GCA | CCC | ACC | AAG | GCA | AAG | AGA | AGA | GTG | GTG | 912 |
| Ile | Glu | Pro | Leu | Gly | Val | Ala | Pro | Thr | Lys | Ala | Lys | Arg | Arg | Val | Val | |
| | | | 290 | | | | | 295 | | | | | 300 | | | |
| CAG | AGA | GAA | AAA | AGA | GCA | GTG | GGA | ATA | GGA | GCT | TTG | TTC | CTT | GGG | TTC | 960 |
| Gln | Arg | Glu | Lys | Arg | Ala | Val | Gly | Ile | Gly | Ala | Leu | Phe | Leu | Gly | Phe | |
| | | | 305 | | | | | 310 | | | | | 315 | | | |
| TTG | GGA | GCA | GCA | GGA | AGC | ACT | ATG | GGC | GCA | GCC | TCA | ATG | ACG | CTG | ACG | 1008 |
| Leu | Gly | Ala | Ala | Gly | Ser | Thr | Met | Gly | Ala | Ala | Ser | Met | Thr | Leu | Thr | |
| | 320 | | | | | 325 | | | | | 330 | | | | | |
| GTA | CAG | GCC | AGA | CAA | TTA | TTG | TCT | GGT | ATA | GTG | CAG | CAG | CAG | AAC | AAT | 1056 |
| Val | Gln | Ala | Arg | Gln | Leu | Leu | Ser | Gly | Ile | Val | Gln | Gln | Gln | Asn | Asn | |
| 335 | | | | | 340 | | | | | 345 | | | | | 350 | |
| TTG | CTG | AGG | GCT | ATT | GAG | GCG | CAA | CAG | CAT | CTG | TTG | CAA | CTC | ACA | GTC | 1104 |
| Leu | Leu | Arg | Ala | Ile | Glu | Ala | Gln | Gln | His | Leu | Leu | Gln | Leu | Thr | Val | |
| | | | | 355 | | | | 360 | | | | | 365 | | | |
| TGG | GGC | ATC | AAG | CAG | CTC | CAA | GCA | AGA | ATC | CTA | GCT | GTG | GAA | AGA | TAC | 1152 |
| Trp | Gly | Ile | Lys | Gln | Leu | Gln | Ala | Arg | Ile | Leu | Ala | Val | Glu | Arg | Tyr | |
| | | | 370 | | | | | 375 | | | | | 380 | | | |
| CTA | AAG | GAT | CAA | CAG | CTC | CTA | GGG | ATT | TGG | GGT | TGC | TCT | GGA | AAA | CTC | 1200 |
| Leu | Lys | Asp | Gln | Gln | Leu | Leu | Gly | Ile | Trp | Gly | Cys | Ser | Gly | Lys | Leu | |
| | | 385 | | | | | 390 | | | | | 395 | | | | |
| ATT | TGC | ACC | ACT | GCT | GTG | CCT | TGG | AAT | GCT | AGT | TGG | AGT | AAT | AAA | TCT | 1248 |
| Ile | Cys | Thr | Thr | Ala | Val | Pro | Trp | Asn | Ala | Ser | Trp | Ser | Asn | Lys | Ser | |
| | 400 | | | | | 405 | | | | | 410 | | | | | |
| CTG | GAA | CAG | ATC | TGG | AAT | CAC | ACG | ACC | TGG | ATG | GAG | TGG | GAC | AGA | GAA | 1296 |
| Leu | Glu | Gln | Ile | Trp | Asn | His | Thr | Thr | Trp | Met | Glu | Trp | Asp | Arg | Glu | |
| 415 | | | | | 420 | | | | | 425 | | | | | 430 | |
| ATT | AAC | AAT | TAC | ACA | AGC | TTA | ATA | CAC | TCC | TTA | ATT | GAA | GAA | TCG | CAA | 1344 |
| Ile | Asn | Asn | Tyr | Thr | Ser | Leu | Ile | His | Ser | Leu | Ile | Glu | Glu | Ser | Gln | |
| | | | | 435 | | | | 440 | | | | | 445 | | | |
| AAC | CAG | CAA | GAA | AAG | AAT | GAA | CAA | GAA | TTA | TTG | GAA | TTA | GAT | AAA | TGG | 1392 |
| Asn | Gln | Gln | Glu | Lys | Asn | Glu | Gln | Glu | Leu | Leu | Glu | Leu | Asp | Lys | Trp | |
| | | | | 450 | | | | 455 | | | | | 460 | | | |
| GCA | AGT | TTG | TGG | AAT | TGG | TTT | AAC | ATA | ACA | AAT | TGG | CTG | TGG | TAT | ATA | 1440 |
| Ala | Ser | Leu | Trp | Asn | Trp | Phe | Asn | Ile | Thr | Asn | Trp | Leu | Trp | Tyr | Ile | |
| | | | 465 | | | | | 470 | | | | | 475 | | | |
| AAA | TTA | TTC | ATA | ATG | ATA | GTA | GGA | GGC | TTG | GTA | GGT | TTA | AGA | ATA | GTT | 1488 |
| Lys | Leu | Phe | Ile | Met | Ile | Val | Gly | Gly | Leu | Val | Gly | Leu | Arg | Ile | Val | |
| | | | 480 | | | | | 485 | | | | | 490 | | | |
| TTT | GCT | GTA | CTT | TCT | ATA | GTG | AAT | AGA | GTT | AGG | CAG | GGA | TAT | TCA | CCA | 1536 |
| Phe | Ala | Val | Leu | Ser | Ile | Val | Asn | Arg | Val | Arg | Gln | Gly | Tyr | Ser | Pro | |
| 495 | | | | | 500 | | | | | 505 | | | | | 510 | |

```
TTA  TCG  TTT  CAG  ACC  CAC  CTC  CCA  ATC  TCGAG                                          1568
Leu  Ser  Phe  Gln  Thr  His  Leu  Pro  Ile
               515
```

( 2 ) INFORMATION FOR SEQ ID NO:8:

( i ) SEQUENCE CHARACTERISTICS:
        ( A ) LENGTH: 519 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Cys  Pro  Lys  Val  Ser  Phe  Glu  Pro  Ile  Pro  Ile  His  Tyr  Cys  Ala  Pro
 1              5                   10                            15

Ala  Gly  Phe  Ala  Ile  Leu  Lys  Cys  Asn  Asn  Lys  Thr  Phe  Asn  Gly  Thr
               20                   25                            30

Gly  Pro  Cys  Thr  Asn  Val  Ser  Thr  Val  Gln  Cys  Thr  His  Gly  Ile  Arg
          35                        40                       45

Pro  Val  Val  Ser  Thr  Gln  Leu  Leu  Asn  Gly  Ser  Leu  Ala  Glu  Glu
     50                        55                   60

Glu  Val  Val  Ile  Arg  Ser  Val  Asn  Phe  Thr  Asp  Asn  Ala  Lys  Thr  Ile
 65                       70                  75                             80

Ile  Val  Gln  Leu  Asn  Thr  Ser  Val  Glu  Ile  Asn  Cys  Thr  Arg  Pro  Asn
               85                       90                            95

Asn  Asn  Thr  Arg  Lys  Arg  Ile  Arg  Ile  Gln  Arg  Gly  Pro  Gly  Arg  Ala
              100                      105                      110

Phe  Val  Thr  Ile  Gly  Lys  Ile  Gly  Asn  Met  Arg  Gln  Ala  His  Cys  Asn
              115                      120                      125

Ile  Ser  Arg  Ala  Lys  Trp  Asn  Asn  Thr  Leu  Lys  Gln  Ile  Asp  Ser  Lys
     130                      135                      140

Leu  Arg  Glu  Gln  Phe  Gly  Asn  Asn  Lys  Thr  Ile  Ile  Phe  Lys  Gln  Ser
145                           150                      155                  160

Ser  Gly  Gly  Asp  Pro  Glu  Ile  Val  Thr  His  Ser  Phe  Asn  Cys  Gly  Gly
                    165                      170                      175

Glu  Phe  Phe  Tyr  Cys  Asn  Ser  Thr  Gln  Leu  Phe  Asn  Ser  Thr  Trp  Phe
               180                      185                      190

Asn  Ser  Thr  Trp  Ser  Thr  Glu  Gly  Ser  Asn  Asn  Thr  Glu  Gly  Ser  Asp
          195                      200                      205

Thr  Ile  Thr  Leu  Pro  Cys  Arg  Ile  Lys  Gln  Ile  Ile  Asn  Met  Trp  Gln
     210                      215                      220

Lys  Val  Gly  Lys  Ala  Met  Tyr  Ala  Pro  Pro  Ile  Ser  Gly  Gln  Ile  Arg
225                           230                      235                  240

Cys  Ser  Ser  Asn  Ile  Thr  Gly  Leu  Leu  Leu  Thr  Arg  Asp  Gly  Gly  Asn
                    245                      250                      255

Ser  Asn  Asn  Glu  Ser  Glu  Ile  Phe  Arg  Leu  Gly  Gly  Gly  Asp  Met  Arg
               260                      265                      270

Asp  Asn  Trp  Arg  Ser  Glu  Leu  Tyr  Lys  Tyr  Lys  Val  Val  Lys  Ile  Glu
          275                      280                      285

Pro  Leu  Gly  Val  Ala  Pro  Thr  Lys  Ala  Lys  Arg  Arg  Val  Val  Gln  Arg
     290                      295                      300

Glu  Lys  Arg  Ala  Val  Gly  Ile  Gly  Ala  Leu  Phe  Leu  Gly  Phe  Leu  Gly
305                           310                      315                  320

Ala  Ala  Gly  Ser  Thr  Met  Gly  Ala  Ala  Ser  Met  Thr  Leu  Thr  Val  Gln
                    325                      330                      335

Ala  Arg  Gln  Leu  Leu  Ser  Gly  Ile  Val  Gln  Gln  Gln  Asn  Asn  Leu  Leu
```

|   |   | 340 |   |   |   |   | 345 |   |   |   |   | 350 |   |   |   |
|---|---|---|---|---|---|---|---|---|---|---|---|---|---|---|---|
| Arg | Ala | Ile 355 | Glu | Ala | Gln | Gln | His 360 | Leu | Leu | Gln | Leu | Thr 365 | Val | Trp | Gly |
| Ile | Lys 370 | Gln | Leu | Gln | Ala | Arg 375 | Ile | Leu | Ala | Val | Glu 380 | Arg | Tyr | Leu | Lys |
| Asp 385 | Gln | Gln | Leu | Leu | Gly 390 | Ile | Trp | Gly | Cys | Ser 395 | Gly | Lys | Leu | Ile | Cys 400 |
| Thr | Thr | Ala | Val | Pro 405 | Trp | Asn | Ala | Ser | Trp 410 | Ser | Asn | Lys | Ser | Leu 415 | Glu |
| Gln | Ile | Trp | Asn 420 | His | Thr | Thr | Trp | Met 425 | Glu | Trp | Asp | Arg | Glu 430 | Ile | Asn |
| Asn | Tyr | Thr 435 | Ser | Leu | Ile | His | Ser 440 | Leu | Ile | Glu | Glu | Ser 445 | Gln | Asn | Gln |
| Gln | Glu 450 | Lys | Asn | Glu | Gln | Glu 455 | Leu | Leu | Glu | Leu | Asp 460 | Lys | Trp | Ala | Ser |
| Leu 465 | Trp | Asn | Trp | Phe | Asn 470 | Ile | Thr | Asn | Trp | Leu 475 | Trp | Tyr | Ile | Lys | Leu 480 |
| Phe | Ile | Met | Ile | Val 485 | Gly | Gly | Leu | Val | Gly 490 | Leu | Arg | Ile | Val | Phe 495 | Ala |
| Val | Leu | Ser | Ile 500 | Val | Asn | Arg | Val | Arg 505 | Gln | Gly | Tyr | Ser | Pro 510 | Leu | Ser |
| Phe | Gln | Thr 515 | His | Leu | Pro | Ile |   |   |   |   |   |   |   |   |   |

ENCAPSIDATED RECOMBINANT POLIOVIRUS NUCLEIC ACID AND METHODS OF MAKING AND USING SAME

GOVERNMENT SUPPORT

The work described herein was supported by Public Health Service contract (Mucosal Immunology Group) AI 15128 and Public Health Service grant AI25005 from the National Institutes of Health.

This application is a continuation of U.S. application Ser. No. 08/087,009, filed Jul. 1993, abandoned.

BACKGROUND OF THE INVENTION

The present invention relates to methods of encapsidating a recombinant viral nucleic acid having a foreign nucleotide sequence substituted for the nucleotide sequence of the virus encoding at least a portion of a protein necessary for encapsidation. More particularly, the invention relates to methods and compositions for generating an immune response in a subject by using such a recombinant virus.

Live or attenuated viruses have long been used to stimulate the immune system in a subject. Poliovirus is an attractive candidate system for delivery of antigens to the mucosal immune system because of several biological features inherent to the virus. First, the pathogenesis of the poliovirus is well-studied and the important features identified. The poliovirus is naturally transmitted by an oral-fecal route and is stable in the harsh conditions of the intestinal tract. Primary replication occurs in the oropharynx and gastro-intestinal tract, with subsequent spread to the lymph nodes. Horstmann, D. M. et al. (1959) JAMA 170:1–8. Second, the attenuated strains of poliovirus are safe for humans, and are routinely administered to the general population in the form of the Sabin oral vaccine. The incorporation of foreign genes into the attenuated strains would be an attractive feature that should pose no more of a health risk than that associated with administration of the attenuated vaccines alone. Third, the entire poliovirus has been cloned, the nucleic acid sequence determined, and the viral proteins identified. An infectious cDNA is also available for poliovirus which has allowed further genetic manipulation of the virus. Further, previous studies using the attenuated vaccine strains of poliovirus have demonstrated that a long-lasting systemic and mucosal immunity is generated after administration of the vaccine. Sanders, D. Y. and Cramblett, H. G. (1974) J. Ped. 84:406–408; Melnick, J. (1978) Bull. World Health Organ. 56:21–38; Racaniello, V. R. and Baltimore, D. (1981) Science 214:916–919; Ogra, P. L. (1984) Rev. Infect. Dis. 6:S361–S368.

Recent epidemiological data suggest that worldwide more than seventy percent of infections with human immunodeficiency virus (HIV) are acquired by heterosexual intercourse through mucosal surfaces of the genital tract and rectum. Most HIV vaccines developed to date have been designed to preferentially stimulate the systemic humoral immune system and have relied on immunization with purified, whole human immunodeficiency virus type 1 (HIV-1) and HIV-1 proteins (Haynes, B. F. (May 1993) Science 260:1279–1286.), or infection with a recombinant virus or microbe which expresses HIV-1 proteins (McGhee, J. R., and Mestecky, J. (1992) AIDS Res. Rev. 2:289–312). A general concern with these studies is that the method of presentation of the HIV-1 antigen to the immune system will not stimulate systemic and mucosal tissues to generate effective immunity at mucosal surfaces. Given the fact that the virus most often encounters a mucosal surface during sexual (vaginal or anal) transmission, a vaccine designed to stimulate both the systemic and mucosal immune systems is essential. McGhee, J. R., and Mestecky, J. (1992) AIDS Res. Rev. 2:289–312; Forrest, B. D. (1992) AIDS Research and Human Retroviruses 8:1523–1525.

In 1991, a group of researchers reported the construction and characterization of chimeric HIV-1-poliovirus genomes. Choi, W. S. et al. (June 1991) J. Virol. 65(6):2875–2883. Segments of the HIV-1 proviral DNA containing the gag, pol, and env gene were inserted into the poliovirus cDNA so that the translational reading frame was conserved between the HIV-1 and poliovirus genes. The RNAs derived from the in vitro transcription of the genomes, when transfected into cells, replicated and expressed the appropriate HIV-1 protein as a fusion with the poliovirus P1 protein. Choi, W. S. et al. (June 1991) J. Virol. 65(6):2875–2883. However, since the chimeric HIV-1-poliovirus genomes were constructed by replacing poliovirus capsid genes with the HIV-1 gag, pol, or env genes, the chimeric HIV-1-genomes were not capable of encapsidation after introduction into host cells. Choi, W. S. et al. (June 1991) J. Virol. 65(6):2875–2883. Furthermore, attempts to encapsidate the chimeric genome by cotransfection with the poliovirus infectious RNA yielded no evidence of encapsidation. Choi, W. S. et al. (June 1991) J. Virol. 65(6):2875–2883. Without encapsidation, the chimeric poliovirus genome cannot be employed to deliver immunogenic proteins to the immune system, and thus is of little practical use.

In 1992, another group of researchers reported the encapsidation of a poliovirus replicon which incorporated the reporter gene, chloramphenicol acetyltransferase (CAT), in place of the region coding for capsid proteins VP4, VP2, and a portion of VP3 in the genome of poliovirus type 3. Percy, N. et al. (Aug. 1992) J. Virol. 66(8):5040–5046. Encapsidation of the poliovirus replicon was accomplished by first transfecting host cells with the poliovirus replicon and then infecting the host cells with type 3 poliovirus. Percy, N. et al. (Aug. 1992) J. Virol 66(8):5040, 5044. The formation of the capsid around the poliovirus genome is believed to be the result of interactions between capsid proteins and the poliovirus genome. Therefore, it is likely that the yield of encapsidated viruses obtained by Percy et al. consisted of a mixture of encapsidated poliovirus replicons and encapsidated nucleic acid from the type 3 poliovirus. The encapsidated type 3 poliovirus most likely represents a greater proportion of the encapsidated viruses than does the encapsidated poliovirus replicons. The Percy et al. method of encapsidating a poliovirus replicon is, therefore, an inefficient system for producing encapsidated recombinant poliovirus nucleic acid.

Accordingly, it would be desirable to provide a method of encapsidating a recombinant poliovirus genome which results in a stock of encapsidated viruses substantially composed of the recombinant poliovirus genome. Such a method would enable the efficient production of encapsidated poliovirus nucleic acid for use in compositions for stimulating an immune response to foreign proteins encoded by the recombinant poliovirus genome.

SUMMARY OF THE INVENTION

The present invention pertains to a method of encapsidating a recombinant poliovirus nucleic acid to obtain a yield of encapsidated viruses which substantially comprises encapsidated recombinant poliovirus nucleic acid. The method of encapsidating a recombinant poliovirus nucleic acid includes providing a recombinant poliovirus nucleic acid which lacks the nucleotide sequence encoding at least a portion of a protein necessary for encapsidation and an expression vector lacking an infectious poliovirus genome, the nucleic acid of which encodes at least a portion of one protein necessary for encapsidation; contacting a host cell with the recombinant poliovirus nucleic acid and the expression vector under conditions appropriate for introduction of the recombinant poliovirus nucleic acid and the expression vector into the host cell; and obtaining a yield of encapsidated viruses which substantially comprises an encapsidated recombinant poliovirus nucleic acid. The nucleic acid of the expression vector does not interact with the capsid proteins or portions of capsid proteins which it encodes, thereby allowing encapsidation of the recombinant poliovirus nucleic acid and avoiding encapsidation of the nucleic acid of the expression vector. The invention further pertains to encapsidated recombinant poliovirus nucleic acids produced by the method of this invention.

In a preferred method of encapsidating a recombinant poliovirus nucleic acid, a mammalian host cell is contacted with a recombinant poliovirus nucleic acid and a vaccinia virus. The VP2 and VP3 genes of the P1 capsid precursor region of the poliovirus are preferably replaced by a foreign nucleotide sequence encoding, in an expressible form, a protein or fragment thereof, such as an immunogenic protein. The nucleic acid of the vaccinia virus preferably encodes the poliovirus capsid precursor protein P1. Because the recombinant poliovirus nucleic acid does not compete with the vaccinia viral nucleic acid for the poliovirus capsid proteins, a yield of encapsidated viruses which substantially comprises an encapsidated poliovirus nucleic acid is obtained. Further, the resulting encapsidated recombinant poliovirus nucleic acid is able to direct expression of the foreign protein or fragment thereof.

The present invention also pertains to a composition for stimulating an immune response to an immunogenic protein or fragment thereof and a method for stimulating the immune response by administering the composition to a subject. The composition contains an encapsidated recombinant poliovirus nucleic acid, in a physiologically acceptable carrier, which encodes an immunogenic protein or fragment thereof and directs expression of the immunogenic protein, or fragment thereof. The composition is administered to a subject in an amount effective to stimulate the production of antibodies to the immunogenic protein or fragment thereof.

The invention still further pertains to a method for stimulating an immune response to an immunogenic protein or fragment thereof by generating cells that produce an encapsidated recombinant poliovirus nucleic acid which encodes and directs expression of the immunogenic protein or fragment thereof and a method of stimulating an immune response by implanting the cell and introducing the cells so generated into a subject.

DETAILED DESCRIPTION OF THE INVENTION

Figure 1:
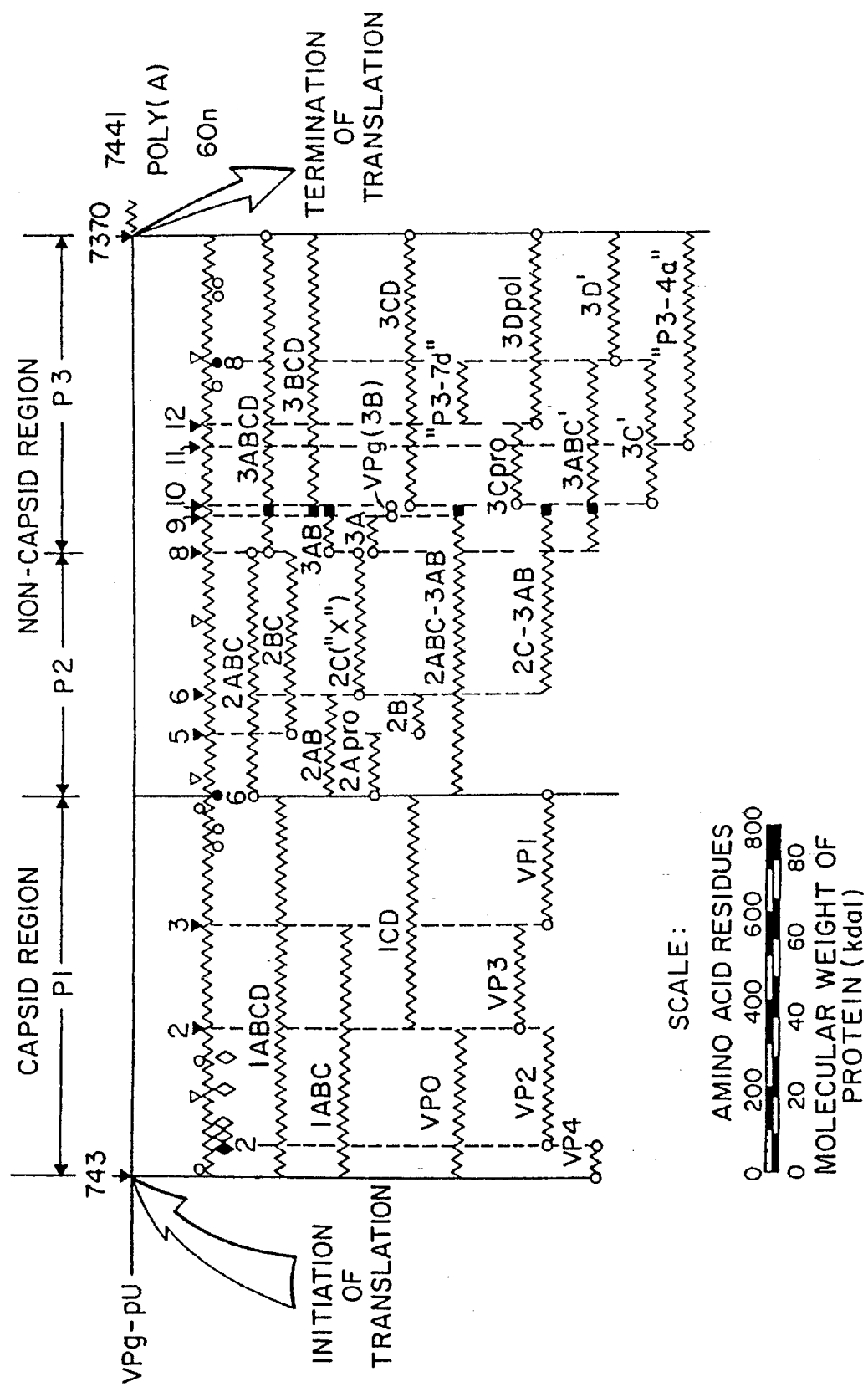
FIG. 1 shows a schematic of the translation and proteolytic processing of the poliovirus polyprotein.

The genome of poliovirus has been cloned and the nucleic acid sequence determined. The genomic RNA molecule is 7433 nucleotides long, polyadenylated at the 3' end and has a small covalently attached viral protein (VPg) at the 5' terminus. Kitamura, N. et al.(1981) *Nature* (London) 291:547–553; Racaniello, V. R. and Baltimore, D. (1981) *Proc. Natl. Acad. Sci. USA* 78:4887–4891. Expression of the poliovirus genome occurs via the translation of a single protein (polyprotein) which is subsequently processed by virus encoded proteases (2A and 3C) to give the mature structural (capsid) and nonstructural proteins. Kitamura, N. et al.(1981) *Nature* (London) 291:547–553; Koch, F. and Koch, G. (1985) The Molecular Biology of Poliovirus (Springer-Verlag, Vienna). Poliovirus replication is catalyzed by the virus-encoded RNA-dependent RNA polymerase ($3D^{pol}$), which copies the genomic RNA to give a complementary RNA molecule, which then serves as a template for further RNA production. Koch, F. and Koch, G. (1985) The Molecular Biology of the Poliovirus (Springer-Verlag, Vienna); Kuhn, R. J. and Wimmer, E. (1987) in D. J. Rowlands et al. (ed.) Molecular Biology of Positive Strand RNA viruses (Academic Press, Ltd., London).

The translation and proteolytic processing of the poliovirus polyprotein is depicted in FIG. 1 which is a figure from Nicklin, M. J. H. et al. (1986) *Bio/Technology* 4:33–42. With reference to the schematic in FIG. 1, the coding region and translation product of poliovirus RNA is divided into three primary regions (P1, P2, and P3), indicated at the top of the figure. The RNA is represented by a solid line and relevant nucleotide numbers are indicated by arrows. Protein products are indicated by waved lines. Cleavage sites are mapped onto the polyprotein (top waved line) as filled symbols; open symbols represent the corresponding sites which are not cleaved. (▼,▽) are QG pairs, (◐) are YG pairs, and (♦,◇) are NS pairs. Cleaved sites are numbered according to the occurrence of that amino-acid pair in the translated sequence. Where the amino acid sequence of a terminus of a polypeptide has been determined directly, an open circle has been added to the relevant terminus.

The mature poliovirus proteins arise by a proteolytic cascade which occurs predominantly at Q-G amino acid pairs. Kitamura, N. et al. (1981) *Nature* (London) 291:547–553; Semler, B. L. et al. (1981) *Proc. Natl. Acad Sci.* USA 78:3763–3468; Semler, B. L. et al. (1981) *Virology* 114:589–594; Palmenberg, A. C. (1990) *Ann. Rev. Microbiol.* 44:603–623. A poliovirus-specific protein, $3C^{pro}$, is the protease responsible for the majority of the protease cleavages. Hanecak, R. et al. (1982) *Proc. Natl. Acad Sci.* USA:79–3973–3977; Hanecak, R. et al. (1984) *Cell* 37:1063–1073; Nicklin, M. J. H. et al. (1986) *Bio/Technology* 4:33–42; Harris, K. L et al. (1990) *Seminars in Virol.* 1:323–333. A second viral protease, $2A^{pro}$, autocatalytically cleaves from the viral polyprotein to release P1, the capsid precursor. Toyoda, H. et al. (1986) Cell 45:761–770. A second, minor cleavage by $2A^{pro}$ occurs within the $3D^{pol}$ to give 3C' and 3D'. Lee, Y. F. and Wimmer, E. (1988) *Virology* 166:404–414. Another role of the $2A^{pro}$ is the shut off of host cell protein synthesis by inducing the cleavage of a cellular protein required for cap-dependent translation. Bernstein, H. D. et al. (1985) *Mol. Cell Biol.* 5:2913–2923; Krausslich, H. G. et al. (1987) *J. Virol.* 61:2711–2718; Lloyd, R. E. et al. (1988)J. Virol. 62:4216–4223.

Previous studies have established that the entire poliovirus genome is not required for RNA replication. Hagino-Yamagishi, K., and Nomoto, A. (1989) *J. Virol.* 63:5386–5392. Naturally occurring defective interfering particles (DIs) of poliovirus have the capacity for replication. Cole, C. N. (1975) *Prog. Med. Virol.* 20:180–207; Kuge, S. et al. (1986) *J. Mol. Biol.* 192:473–487. The common feature of the poliovirus DI genome is a partial deletion of the capsid (P1) region that still maintains the translational reading frame of the single polyprotein through which expression of the entire poliovirus genome occurs. In recent years, the availability of infectious cDNA clones of the poliovirus genome has facilitated further study to define the regions required for RNA replication. Racaniello, V. and Baltimore, D. (1981) *Science* 214:916–919. Specifically, the deletion of 1,782 nucleotides of P1, corresponding to nucleotides 1174 to 2956, resulted in an RNA which can replicate upon transfection into tissue culture cells. Hagino-Yamagishi, K. and Nomoto, A. (1989) *J. Virol.* 63:5386–5392.

Early studies identified three poliovirus types based on reactivity to antibodies. Koch, F. and Koch, G. The Molecular Biology of Poliovirus (Springer-Verlag, Vienna 1985). These three serological types, designated as type I, type II, and type III, have been further distinguished as having numerous nucleotide differences in both the non-coding regions and the protein coding regions. All three strains are suitable for use in the present invention. In addition, there are also available attenuated versions of all three strains of poliovirus. These include the Sabin type I, Sabin type II, and Sabin type III attenuated strains of poliovirus that are routinely given to the population in the form of an oral vaccine. These strains can also be used in the present invention.

The recombinant poliovirus nucleic acid of the present invention lacks the nucleotide sequence encoding at least a portion or a protein necessary for encapsidation of the recombinant poliovirus nucleic acid. The nucleotide sequence that is absent from the recombinant poliovirus nucleic acid can be any sequence at least a portion of which encodes at least a portion of a protein necessary for encapsidation, and the lack of which does not interfere with the ability of the poliovirus nucleic acid to replicate or to translate, in the correct reading frame, the single polyprotein through which expression of the entire poliovirus genome occurs. The recombinant poliovirus nucleic acid can be deoxyribonucleic acid (DNA) or ribonucleic acid (RNA). As the poliovirus genome is comprised of RNA which replicates in the absence of a DNA intermediate, it is typically introduced into a cell in the form of RNA. This avoids integration of the poliovirus genome into that of the host cell.

Proteins or portions of proteins necessary for encapsidation of a recombinant poliovirus nucleic acid include, for example, proteins or portions of proteins that are part of the capsid structure. Examples of such are the proteins encoded by the VP1, VP2, VP3, or VP4 genes of the poliovirus P1 capsid precursor region, the Vpg protein, or those that are necessary for proper processing of structural proteins of the capsid structure, such as the proteases responsible for cleaving the viral polyprotein.

The nucleotide sequence lacking from the recombinant poliovirus nucleic acid can be the result of a deletion and insertion of a foreign gene. Generally, the nucleotide sequence lacking from the recombinant poliovirus nucleic acid is the P1 region of the poliovirus genome or a portion thereof, which is replaced by a foreign gene. The foreign gene preferably is one that encodes, in an expressible form, a foreign protein or fragment thereof. For example, foreign genes that can be inserted into the deleted region of the poliovirus nucleic acid can be those that encode immunogenic proteins. Such immunogenic proteins include, for example, hepatitis B surface antigen, influenza virus hemaglutinin and neuraminidase, human immunodeficiency viral proteins, such as gag, pol, and env, respiratory syncycial virus G protein, bacterial antigens such as fragments of tetanus toxin, diphtheria toxin, and cholera toxin, and mycobacterium tuberculosis protein antigen B. In addition, portions of the foreign genes which encode immunogenic proteins can be inserted into the deleted region of the poliovirus nucleic acid. These genes can encode linear polypeptides consisting of B and T cell epitopes. As these are the epitopes with which B and T cells interact, the polypeptides stimulate an immune response. It is also possible to insert chimeric foreign genes into the deleted region of the poliovirus nucleic acid which encode fusion proteins or peptides consisting of both B cell and T cell epitopes. Similarly, any foreign nucleotide sequence encoding an antigen from an infectious agent could be inserted into the deleted region of the poliovirus nucleic acid.

The foreign gene inserted into the deleted region of the poliovirus nucleic acid can also encode, in an expressible form, immunological response modifiers such as interleukins (e.g. interleukin-1, interleukin-2, interleukin-6, etc.), tumor necrosis factor (e.g. tumor necrosis factor-α, tumor necrosis factor-β), or additional cytokines (granulocyte-monocyte colony stimulating factor, interferon-γ). As an expression system for lymphokines or cytokines, the encapsidated poliovirus nucleic acid encoding the lymphokine or cytokine provides for limited expression (by the length of time it takes for the replication of the genome) and can be locally administered to reduce toxic side effects from systemic administration. In addition, genes encoding antisense nucleic acid, such as antisense RNA, or genes encoding ribozymes (RNA molecules with endonuclease or polymerase activities) can be inserted into the deleted region of the poliovirus nucleic acid. The antisense RNA or ribozymes can be used to modulate gene expression or act as a potential anti-viral agents.

Foreign genes encoding, in an expressible form, cell surface proteins, secretory proteins, or proteins necessary for proper cellular function which supplement a nonexistent, deficient, or nonfunctional cellular supply of the protein can also be inserted into the deleted region of the poliovirus nucleic acid. The nucleic acid of genes encoding secretory proteins comprises a structural gene encoding the desired protein in a form suitable for processing and secretion by the target cell. For example, the gene can be one that encodes appropriate signal sequences which provide for cellular secretion of the product. The signal sequence may be the natural sequence of the protein or exogenous sequences. The structural gene is linked to appropriate genetic regulatory elements required for expression of the gene product by the target cell. These include a promoter and optionally an enhancer element along with the regulatory elements necessary for expression of the gene and secretion of the gene encoded product.

In one embodiment, the foreign genes that are substituted for the VP2 and VP3 capsid genes of the P1 capsid precursor region of the poliovirus correspond to the region of the gag (SEQ ID NO: 3; the sequence of the corresponding gag protein is represented by SEQ ID NO: 4), pol (SEQ ID NO: 5; the sequence of the corresponding pol protein is represented by SEQ ID NO: 6), or env (SEQ ID NO: 7; the sequence of the corresponding env protein is represented by SEQ ID NO: 8) genes of the human immunodeficiency virus type 1 (HIV-1). These genes are typically inserted in the poliovirus between nucleotides 1174 and 2956. The translational reading frame is thus conserved between the HIV-1 genes and the poliovirus genes. The chimeric HIV-1-poliovirus RNA genomes replicate and express the appropriate HIV-1-P1 fusion proteins upon transfection into tissue culture. Choi, W. S. et al. (June 1991) *J. Virol.* 65(6):2875–2883;

Deletion or replacement of the P1 capsid region of the poliovirus genome or a portion thereof results in a poliovirus nucleic acid which is incapable of encapsidating itself. Choi, W. S. et al. (June 1991) *J. Virol.* 65(6):2875–2883. Typically, capsid proteins or portions thereof mediate viral entry into cells. Therefore, poliovirus nucleic acid which is not enclosed in a capsid is not able to enter cells on which there is a poliovirus receptor and is thereby incapable of delivering foreign genes encoding the desired protein to cells. It is necessary for encapsidation and delivery of the foreign genes to cells, therefore, to provide the essential capsid proteins from another source. In the method of this invention, essential poliovirus capsid proteins are provided by an expression vector which is introduced into the host cell along with the recombinant poliovirus nucleic acid. The expression vectors can be introduced into the host cell prior to, concurrently with, or subsequent to the introduction of the recombinant poliovirus nucleic acid.

In a preferred method of encapsidating the recombinant poliovirus nucleic acid, the expression vector is introduced into the host cell prior to the introduction of the recombinant poliovirus nucleic acid. The introduction of the expression vector into the host cell prior to the introduction of the recombinant poliovirus nucleic acid allows the initial expression of the protein or portion of the protein necessary for encapsidation by the expression vector. Previous studies have established that the replication and expression of the poliovirus genes in cells results in the shutoff of host cell protein synthesis which is accomplished by the $2A^{pro}$ protein of poliovirus. Thus, in order for efficient encapsidation, the expression vector must express the protein necessary for encapsidation. In order for this to occur, the expression vector should generally be introduced into the cell prior to the addition of the recombinant poliovirus nucleic acid.

Expression vectors suitable for use in the present invention include plasmids and viruses, the nucleic acids of which encode at least a portion of a protein necessary for encapsidation of the recombinant poliovirus nucleic acid and direct expression of the nucleotide sequence encoding at least a portion of a protein necessary for encapsidation of the recombinant poliovirus nucleic acid. In addition, the nucleic acid of the expression vectors of the present invention does not substantially associate with poliovirus capsid proteins or portions thereof. Therefore, expression vectors of the present invention, when introduced into a host cell along with the recombinant poliovirus nucleic acid, result in a host cell yield of encapsidated viruses which is substantially composed of encapsidated recombinant poliovirus nucleic acid. Generally, the nucleic acid of the expression vector will encode and direct expression of the nucleotide sequence coding for a capsid protein which the recombinant poliovirus nucleic acid is not capable of expressing.

Plasmid expression vectors can typically be designed and constructed such that they contain a gene encoding, in an expressible form, a protein or a portion of a protein necessary for encapsidation of the recombinant poliovirus nucleic acid. Generally, construction of such a plasmid is a standard method and is described in Sambrook, J. et al. Molecular Cloning: A Laboratory Manual, 2nd edition (CSHL Press, Cold Spring Harbor, N.Y. 1989). A plasmid expression vector which expresses a protein or a portion of a protein necessary for encapsidation of the poliovirus nucleic acid is constructed by first positioning the gene to be inserted (e.g. VP1, VP2, VP3, VP4 or the entire P1 region) after a DNA sequence known to act as a promoter when introduced into cells. The gene to be inserted is typically positioned downstream (3') from the promoter sequence. The promoter sequence consists of a cellular or viral DNA sequence which has been previously demonstrated to attract the necessary host cell components required for initiation of transcription. Examples of such promoter sequences include the long terminal repeat (LTR) regions of Rous Sarcoma Virus, the origin of replication for the SV40 tumor virus (SV4-ori), and the promoter sequence for the CMV (cytomegalovirus) immediate early protein. Plasmids containing these promoter sequences are available from any number of companies which sell molecular biology products (e.g. Promega (Madison, Wis.), Stratagene Cloning Systems (LaJolla, Calif.), and Clontech (Palo Alto, Calif.).

Construction of these plasmid expression vectors would require the excising of a DNA fragment containing the gene to be inserted and ligating this DNA fragment into an expression plasmid cut with restriction enzymes that are compatible with those contained on the 5' and 3' ends of the gene to be inserted. Following ligation of the DNA in vitro, the plasmid is transformed into E. coli and the resulting bacteria is plated onto an agar plate containing an appropriate selective antibiotic. The E. coli colonies are then grown and the plasmid DNA characterized for the insertion of the particular gene. To confirm that the gene has been ligated into the plasmid, the DNA sequence of the plasmid containing the insert is determined. The plasmid expression vector can be transfected into tissue culture cells and the protein encoded by the inserted gene expressed.

The conditions under which plasmid expression vectors are introduced into a host cell vary depending on certain factors. These factors include, for example, the size of the nucleic acid of the plasmid, the type of host cell, and the desired efficiency of transfection. There are several methods of introducing the recombinant poliovirus nucleic acid into the host cells which are well-known and commonly employed by those of ordinary skill in the art. These transfection methods include, for example, calcium phosphate-mediated uptake of nucleic acids by a host cell, DEAE-dextran facilitated uptake of nucleic acid by a host cell. Alternatively, nucleic acids can be introduced into cells through electroporation, (Neumann, E. et al. (1982) *EMBO J.* 1:841–845), which is the transport of nucleic acids directly across a cell membrane by means of an electric current or through the use of cationic liposomes (e.g. lipofection, Gibco/BRL (Gaithersburg, Md.)). The methods that will be most efficient in each case are typically determined empirically upon consideration of the above factors.

As with plasmid expression vectors, viral expression vectors can be designed and constructed such that they contain a foreign gene encoding a foreign protein or fragment thereof and the regulatory elements necessary for expressing the foreign protein. Viruses suitable for use in the method of this invention include viruses that contain nucleic acid that does not substantially associate with poliovirus capsid proteins. Examples of such viruses include retroviruses, adenoviruses, and Sindbis virus. Retroviruses, upon introduction into a host cell, establish a continuous cell line expressing a foreign protein. Adenoviruses are large DNA viruses which have a host range in human cells similar to that of poliovirus. Sindbis virus is an RNA virus that replicates, like poliovirus, in the cytoplasm of cells and, therefore, offers a convenient system for expressing poliovirus capsid proteins. A preferred viral expression vector is a vaccinia virus. Vaccinia virus is a DNA virus which replicates in the cell cytoplasm and has a similar host range to that of poliovirus. In addition, vaccinia virus can accommodate large amounts of foreign DNA and can replicate efficiently in the same cell in which poliovirus replicates. A preferred nucleotide sequence that is inserted in the vaccinia is the nucleotide sequence encoding and expressing, upon infection of a host cell, the poliovirus P1 capsid precursor polyprotein.

The construction of this vaccinia viral vector is described by Ansardi, D. C. et al. (Apr. 1991) *J. Virol.* 65(4):2088–2092. Briefly, type I Mahoney poliovirus cDNA sequences were digested with restriction enzyme Nde I, releasing sequences corresponding to poliovirus nucleotides 3382–6427 from the plasmid and deleting the P2 and much of the P3 encoding regions. Two synthetic oligonucleotides, (5'-TAT TAG TAG ATC TG (SEQ ID NO: 1)) and 5'-T ACA GAT GTA CTA A (SEQ ID NO: 2)) were annealed together and ligated into the Nde I digested DNA. The inserted synthetic sequence is places two translational termination codons (TAG) immediately downstream from the codon for the synthetic P1 carboxy terminal tyrosine residue. Thus, the engineered poliovirus sequences encode an authentic P1 protein with a carboxy terminus identical to that generated when $2A^{pro}$ releases the P1 polyprotein from the nascent poliovirus polypeptide. An additional modification was also generated by the positioning of a Sal I restriction enzyme site at nucleotide 629 of the poliovirus genome. This was accomplished by restriction enzyme digest (Bal I) followed by ligation of synthetic Sal I linkers. The DNA fragment containing the poliovirus P1 gene was subcloned into the vaccinia virus recombination plasmid, pSC11. Chackrabarti, S. et al. (1985) *Mol. Cell Biol.* 5:3403–3409. Coexpression of beta-galactosidase provides for visual screening of recombinant virus plaques.

The entry of viral expression vectors into host cells generally requires addition of the virus to the host cell media followed by an incubation period during which the virus enters the cell. Incubation conditions, such as the length of incubation and the temperature under which the incubation is carded out, vary depending on the type of host cell and the type of viral expression vector used. Determination of these parameters is well known to those having ordinary skill in the art. In most cases, the incubation conditions for the infection of cells with viruses typically involves the incubation of the virus in serum-free medium (minimal volume) with the tissue culture cells at either room temperature or 37° C. for a minimum of thirty minutes. For some viruses, such as retroviruses, a compound to facilitate the interaction of the virus with the host cell is added. Examples of such infection facilitators include polybrine and DEAE.

A host cell useful in the present invention is one into which both a recombinant poliovirus nucleic acid and an expression vector can be introduced. Common host cells are mammalian host cells, such as, for example, HeLa cells (ATCC Accession No. CCL 2), HeLa S3 (ATCC Accession No. CCL 2.2), the African Green Monkey cells designated BSC-40 cells, which are derived from BSC-1 cells (ATCC Accession No. CCL 26), and HEp-2 cells (ATCC Accession No. CCL 23). Because the recombinant poliovirus nucleic acid is encapsidated prior to serial passage, host cells for such serial passage are preferably permissive for poliovirus replication. Cells that are permissive for poliovirus replication are cells that become infected with the recombinant poliovirus nucleic acid, allow viral nucleic acid replication, expression of viral proteins, and formation of progeny virus articles. In vitro, poliovirus causes the host cell to lyse. However, in vivo the poliovirus may not act in a lytic fashion. Nonpermissive cells can be adapted to become permissive cells, and such cells are intended to be included in the category of host cells which can be used in this invention. For example, the mouse cell line L929, a cell line normally nonpermissive for poliovirus replication, has been adapted to be permissive for poliovirus replication by transfection with the gene encoding the poliovirus receptor. Mendelsohn, C. L. et al. (1989) *Cell* 56:855–865; Mendelsohn, C. L. et al. (1986) *Proc. Natl. Acad Sci.* USA 83:7845–7849.

The encapsidated recombinant poliovirus nucleic acid of the invention can be used in a composition for stimulating a mucosal as well as a systemic immune response to the foreign protein encoded and expressed by the encapsidated recombinant poliovirus nucleic acid in a subject. Examples of genes encoding proteins that can be inserted into the poliovirus nucleic acid are described above. The mucosal immune response is an important immune response because it offers a first line of defense against infectious agents, such an human immunodeficiency virus, which can enter host cells via mucosal cells. At least a portion of a capsid protein of the encapsidated recombinant poliovirus nucleic acid is supplied by an expression vector which lacks an infectious poliovirus genome. Expression vectors suitable for supplying a capsid protein or a portion thereof are described above. Upon administration of the encapsidated recombinant poliovirus nucleic acid, the subject will generally respond to the immunizations by producing both anti-poliovirus antibodies and antibodies to the foreign protein or fragment thereof which is expressed by the recombinant poliovirus nucleic acid. The recombinant poliovirus nucleic acid, in either its DNA or RNA form, can also be used in a composition for stimulating a systemic and a mucosal immune response in a subject. Administration of the RNA form of the recombinant poliovirus nucleic acid is preferred as it typically does not integrate into the host cell genome.

The encapsidated recombinant poliovirus nucleic acid or the non-encapsidated recombinant poliovirus nucleic acid can be administered to a subject in a physiologically acceptable carrier and in an amount effective to stimulate an immune response to at least the foreign protein or fragment thereof for which the recombinant poliovirus nucleic acid encodes and directs expression. Typically, a subject will be immunized through an initial series of injections (or administration through one of the other routes described below) and subsequently given boosters to increase the protection afforded by the original series of administrations. The initial series of injections and the subsequent boosters are administered in such doses and over such a period of time as is necessary to stimulate an immune response in a subject.

Physiologically acceptable carriers suitable for injectable use include sterile aqueous solutions (where water soluble) or dispersions and sterile powders for the extemporaneous preparation of sterile injectable solutions or dispersions. In all cases, the composition must be sterile and must be fluid to the extent that easy syringability exists. The composition must further be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, asorbic acid, thimerosal, and the like.

Sterile injectable solutions can be prepared by incorporating the encapsidated recombinant poliovirus nucleic acid in the required amount in an appropriate solvent with one or a combination of ingredients enumerated above, as required, followed by filtered sterilization.

When the encapsidated or nonencapsidated recombinant poliovirus nucleic acid is suitably protected, as described above, the protein may be orally administered, for example, with an inert diluent or an assimilable edible carrier. The protein and other ingredients may also be enclosed in a hard or soft shell gelatin capsule, compressed into tablets, or incorporated directly into the individual's diet. For oral therapeutic administration, the active compound may be incorporated with excipients and used in the form of ingestible tablets, buccal tablets, troches, capsules, elixirs, suspensions, syrups, wafers, and the like.

As used herein "physiologically acceptable carrier" includes any and all solvents, dispersion media, coatings, antibacterial and antifungal agents, isotonic and absorption delaying agents, and the like. The use of such media and agents for physiologically active substances is well known in the art. Except insofar as any conventional media or agent is incompatible with the active compound, use thereof in the therapeutic compositions is contemplated.

Subjects who can be treated by the method of this invention include living organisms, e.g. mammals, susceptible to infectious diseases. Agents that initiate the infectious disease include microorganisms such as viruses and bacteria. Examples of subjects include humans, monkeys, dogs, cats, rats, and mice.

The amount of the immunogenic composition which can stimulate an immune response in a subject can be determined on an individual basis and will be based, at least in part, on consideration of the activity of the specific immunogenic composition used. Further, the effective amounts of the immunogenic composition may vary according to the age, sex, and weight of the subject being treated. Thus, an effective amount of the immunogenic composition can be determined by one of ordinary skill in the art employing such factors as described above using no more than routine experimentation.

The immunogenic composition is administered through a route which allows the composition to perform its intended function of stimulating an immune response to the protein encoded by the recombinant poliovirus nucleic acid. Examples of routes of administration which may be used in this method include parenteral (subcutaneous, intravenous, intramuscular, intra-arterial, intraperitoneal, intrathecal, intracardiac, and intrasternal), enteral administration (i.e. administration via the digestive tract, e.g. oral, intragastric, and intrarectal administration), and mucosal administration. It is important to note that the vaccine strains of poliovirus are routinely tested for attenuation by intramuscular and intracerebral injection into monkeys. Thus, it would probably pose no associated health risk if the recombinant poliovirus nucleic acid was given parenterally. Depending on the route of administration, the immunogenic composition may be coated with or in a material to protect it from the natural conditions which may detrimentally affect its ability to perform its intended function.

Cells that produce the encapsidated poliovirus nucleic acids of the present invention can be introduced into a subject, thereby stimulating an immune response to the foreign protein or fragment thereof encoded by the recombinant poliovirus nucleic acid. Generally, the cells that are introduced into the subject are first removed from the subject and contacted ex vivo with both the recombinant poliovirus nucleic acid and an expression vector as described above to generate modified cells that produce the foreign protein or fragment thereof. The modified cells that produce the foreign protein or fragment thereof can then be reintroduced into the subject by, for example injection or implantation. Examples of cells that can be modified by this method and injected into a subject include peripheral blood mononuclear cells, such as B cells, T cells, monocytes and macrophages. Other cells, such as cutaneous cells and mucosal cells can be modified and implanted into a subject.

The invention is further illustrated by the following non-limiting examples. The contents of all references and issued patents cited throughout this application are expressly incorporated herein by reference.

EXAMPLE 1

Materials and Methods.

All chemicals were purchased from Sigma Chemical Co. (St. Louis, Mo.). Restriction enzymes were obtained from New England Bio-labs (Beverly, Mass.). Tissue culture media was purchased from Gibco/BRL Co. (Gaithersburg, Md.). $^{35}$S Translabel (methionine-cystine) and methionine-cystine-free Dulbecco modified Eagle medium (DMEM) were purchased from ICN Biochemicals (Irvine, Calif.). T7 RNA polymerase was prepared in this laboratory by the method of Grodberg and Dunn. Grodberg, J. and Dunn, J. J. (1988) *J. Bacteriol.* 170:1245–1253.

Tissue culture cells and viruses

HeLa (human cervical carcinoma) and BSC-40 cells (African green monkey kidney cells) were grown in DMEM supplemented with 5% A-γ newborn calf serum and 5% fetal calf serum (complete medium). The stock of the poliovirus type 1 Mahoney used in this study was derived from transfection of an infectious cDNA clone obtained from B. Semler, University of California at Irvine. Semler, B. L. et al. (1984) *Nucleic Acids* Res. 12:5123–5141. The stock of type 1 Sabin poliovirus was obtained from the American Type Culture Collection (ATCC Accession No. VR-192). Wild-type vaccinia virus (wt VV) strain WR and the recombinant vaccinia virus VV-P1, which express the poliovirus P1 capsid precursor protein, have been previously described. Ansardi, D. C. et al. (1991) *J. Virol.* 65:2088–2092. Antisera to HIV-1 reverse transcriptase (RT) and HIV-1 p25/24 Gag (Steimer, K. S. et al. (1986) *Virology* 150:283–290) were obtained through the AIDS Research and Reference Reagent Program (Rockville, Md.). Pooled AIDS patient sera was obtained from the Center for AIDS Research, University of Alabama at Birmingham.

In vitro transcription reaction

The in vitro transcription reactions were performed by using T7 RNA polymerase as described previously. Choi, W. S. et al (1991)*J. Virol.* 65:2875–2883. Prior to in vitro transcription, DNA templates were linearized by restriction enzyme digestion, followed by successive phenol-chloroform (1:1) chloroform extractions and ethanol precipitation. Reaction mixtures (100 μl) contained 1 to 5 μg of linearized DNA template, 5× transcription buffer (100 mM Tris [pH 7.7], 50 mM $MgCl_2$, 20 mM spermidine, 250 mM NaCl), 10 mM dithiotheritol, 2 mM each GTP, UTP, ATP, and CTP, 40 U of recombinant RNasin (Promega, Madison, Wis.), and approximately 5 μg of purified T7 RNA polymerase per reaction mixture. After 60 min at 37° C., 5% of the in vitro-synthesized RNA was analyzed by agarose gel electrophoresis.

Encapsidation and serial passage of recombinant poliovirus nucleic acids by VV-P1

HeLa cells were infected with 20 PFU of VV-P1 (a recombinant virus which expresses the poliovirus capsid precursor protein P1) or wild type (wt) VV per cell. After 2 hours of infection, the cells were transfected (by using DEAE-dextran [500,000 Da] as a facilitator) with RNA transcribed in vitro from the chimeric HIV-1 poliovirus genomes as previously described. Choi, W. S. et al. (1991) *J. Virol.* 65:2875–2883. The cultures were harvested at 24 hours posttransfection. The cells were lysed with Triton X-100 at a concentration of 1%, treated with RNase A, and clarified by low-speed centrifugation at 14,000×g for 20 min at 4° C. as described previously. Li, G. et al. (1991) J. Virol. 65:6714–6723. The supernatants were adjusted to 0.25% sodium dodecyl sulfate (SDS), overlaid on a 30% sucrose cushion (30% sucrose, 30 mM Tris [pH8.0], 1% Triton X-100, 0.1M NaCl), and centrifuged in a Beckman SW55Ti rotor at 45,000 rpm for 1.5h. The pelleting procedure described above has been demonstrated to be effective for the removal of infectious vaccinia virus to below detectable levels. The supernatant was discarded, and the pellet was washed by recentrifugation for an additional 1.5 hours in a low salt buffer (30 mM Tris [pH 8.0], 0.1M NaCl). The pellets were then resuspended in complete DMEM and designated passage 1 of the recombinant poliovirus nucleic acids encapsidated by VV-P1.

For serial passage of the encapsidated recombinant poliovirus nucleic acids, BSC-40 cells were infected with 20 PFU of VV-P1 per cell. At 2 hours postinfection, the cells were infected with passage 1 of the encapsidated recombinant poliovirus nucleic acids. The cultures were harvested at 24 hours postinfection by three successive freeze-thaws, sonicated, and clarified by centrifugation at 14,000×g for 20 min. The supernatants were then stored at −70° C. or used immediately for additional passages following the same procedure Metabolic labeling and immunoprecipitation of viral proteins To metabolically label viral proteins from infected-transfected or infected cells, the cultures were starved for methionine-cystine at 6 hours postinfection by incubation in DMEM minus methionine-cystine for 30 minutes. At the end of this time, $^{35}$S Translabel was added for an additional hour. Cultures were then processed for immunoprecipitation of viral proteins by lysing the cells with radioimmunoprecipitation assay (RIPA) buffer (150 mM NaCl, 10 mM Tris [pH 7.8], 1% Triton X-100, 1% sodium deoxycholate, 0.2% SDS). Following centrifugation at 14,000×g for 10 min to pellet any debris, designated antibodies were added to the supernatants, which were incubated at 4° C. rocking for 24 hours. The immunoprecipitates were collected by addition of 100 μl of protein A-Sepharose (10% [wt/vol] in RIPA buffer). After 1 hour of rocking at room temperature, the protein A-Sepharose beads were collected by brief configuration and washed three times with RIPA buffer. The bound material was eluted by boiling for 5 minutes in gel sample buffer (50 mM Tris [pH 6.8], 5% SDS, 10% glycerol, 0.01% bromophenol blue, 10% β-mercaptoethanol). The proteins were analyzed by SDS polyacrylamide gel electrophoresis, and radiolabeled proteins were visualized by fluorography.

Nucleic acid hybridization

RNA from a stock of recombinant poliovirus nucleic acids encapsidated by VV-P1 was analyzed by Northern (RNA) blotting. Stocks of encapsidated recombinant poliovirus nucleic acids at passage 14 and a high-titer stock of type 1 Mahoney poliovirus were subjected to RNase A treatment and overlaid on 30% sucrose cushion (30% sucrose, 30 mM Tris [pH 8.0], 1% Triton X-100, 0.1M NaCl). The samples were centrifuged in a Beckman SW55Ti rotor at 45,000 rpm for 1.5 h. Pelleted virions were resuspended in TSE buffer (10 mM Tris-HCl [pH 8.0], 50 mM EDTA) and adjusted to 1% SDS and 1% β-mercaptoethanol as previously described. Rico-Hesse, R. et al. (1987) *Virology* 160:311–322. The resuspended virions were disrupted by extraction three times with phenol-chloroform equilibrated to acidic buffer and one time with chloroform. The extracted RNA was precipitated with 0.2M $LiCl_2$, and 2.5 volumes 100% ethanol. The RNA was denatured and separated on a formaldehyde-agarose gel. The RNA was then transferred from the gel to a nitrocellulose filter by capillary elution (Sambrook, J. et al. (1989) Molecular Cloning: A Laboratory Manual, 2nd edition (Cold Spring Harbor Laboratory Press, N.Y.)) and crosslinked by using a UV Stratalinker (Stratagene, LaJolla, Calif.). The conditions used for prehybridization, hybridization, and washing of RNA immobilized on filters were previously described (Sambrook, J. et al. (1989) Molecular Cloning: A Laboratory Manual, 2nd edition (Cold Spring Harbor Laboratory Press, N.Y.)). Briefly, the blot was prehybridized in hybridization buffer (50% deionized formamide, 6×SSC [1×SSC is 0.15M NaCl plus 0.015M sodium citrate], 1% SDS, 0.1% Tween 20, 100 μg of yeast tRNA per ml). The blot was then incubated in hybridization buffer containing $10^6$ cpm of a [$^{32}$P] UTP-labeled riboprobe complementary to nucleotides 671 to 1174 of the poliovirus genome (Choi, W. S. et al (1991) *J. Virol.* 65:2875–2883) per ml. After hybridization, the blot was washed two times with 0.1×SSC-0.1% SDS at room temperature and one time at 65° C. The blot was then exposed to X-ray film with an intensifying screen.

Neutralization of the recombinant poliovirus nucleic acids encapsidated by VV-P1 using anti-poliovirus antibodies For antibody neutralization, encapsidated recombinant poliovirus nucleic acids at passage 9 were pelleted by ultracentrifugation and resuspended in 250 μl of phosphate-buffered saline (pH 7.0)–0.1% bovine serum albumin. Samples were preincubated with 25 μl of either rabbit anti-poliovirus type 1 Mahoney antisera or preimmune sera per sample at 37° C. for 2 hours. Neutralization experiments were conducted on the basis of the results of preliminary experiments analyzing the capacity of anti-poliovirus antisera to prevent infection of cells by $10^6$ total PFU of poliovirus trader the experimental conditions. The preincubated samples were then analyzed for protein expression by infection of BSC-40 cells which were metabolically labeled at 6 hours postinfection followed by immunoprecipitation of viral proteins.

Encapsidation of the recombinant poliovirus nucleic acids by type 1 Sabin poliovirus BSC-40 cells were coinfected with 10 PFU of type 1 Sabin poliovirus and a stock of encapsidated recombinant poliovirus nucleic acids (passage 14) per cell. The infected cells were harvested at 24 hours postinfection by three successive freeze-thaws, sonicated and clarified by centrifugation at 14,000×g for 20 minutes as described previously (Li, G., et al. *J. Virol.* 65:6714–6723). Approximately one-half of the supernatant was used for serial passaging by reinfection of BSC-40 cells. After 24 hours, the cultures were harvested as described above, and the procedure was repeated for an additional 10 serial passages.

Results

Expression of chimeric HIV-1-poliovirus genomes in VV-P1-infected cells

The construction and characterization of chimeric HIV-1 poliovirus nucleic acid in which the HIV-1 gag or pot gene was substituted for VP2 and VP3 regions of the poliovirus P1 protein in the infectious cDNA of poliovirus have previously been described. Choi, W. S. et al (1991)*J. Virol.* 65:2875–2883 (FIG. 2). FIG. 2 shows chimeric HIV-1-poliovirus genomes containing regions of the HIV-1 gag or pol gene substituted for the poliovirus P1 gene. Details of the construction of plasmids pT7-IC-GAG 1 and pT7-IC-POL have been described by Choi et al. and were presented as pT7IC-NheI-gag and pT7IC-NheI-pol, respectively. To construct pT7-IC-GAG 2, a unique SmaI site was created at nucleotide 1580 of the infectious cDNA or poliovirus, and the HIV-1 gag sequences were subcloned between nucleotides 1580 and 2470. Insertion of the HIV-1 genes maintains the translational reading frame with VP4 and VP1. In vitro transcription from these plasmids generates full-length RNA transcripts (linearized with SalI). Transfection of full-length transcripts into HeLa cells results in expression of the poliovirus 3CD protein, a fusion protein between the $3C^{pro}$ and the $3D^{pol}$ proteins with a molecular mass of 72 kDa. The molecular masses of the HIV-1-P1 fusion proteins are indicated. In previous studies, transfection of these chimeric RNA genomes into type 1 Mahoney poliovirus-infected cells did not result in encapsidation of these RNA genomes (Choi, W. S. et al (1991)*J. Virol.* 65:2875–2883). Under the experimental conditions used, it was possible that the recombinant poliovirus nucleic acid did not efficiently compete with wild-type RNA genomes for capsid proteins. To circumvent this problem, a recombinant vaccinia virus (VV-P1) which expresses the poliovirus capsid precursor protein P1 upon infection was used, since recent studies have shown that in cells coinfected with VV-P1 and poliovirus, P1 protein expressed from VV-P1 can enter the encapsidation pathways of wild type poliovirus.

Protein expression from the recombinant poliovirus nucleic acid transfected into cells previously infected with the recombinant vaccinia virus VV-P1 was analyzed. (FIG. 3 ) FIG. 3 shows an analysis of $3D^{pol}$ and HIV-1-P1 fusion protein expression from cells infected with VV-P1 and transfected with recombinant poliovirus nucleic acid RNAs. Cells were infected with VV-P1 at a multiplicity of infection of 20. At 2 hours postinfection, cells were transfected with RNA derived from in vitro transcription of the designated plasmids. Cells were metabolically labeled and cells extracts were incubated with anti-$3D^{pol}$ antibodies (lanes 1 to 5), pooled AIDS patient sera (lanes 6 to 8), or anti-RT antibodies (lane 9), and immunoreactive proteins were analyzed on SDS-polyacrylamide gels. Lanes: 1, cells infected with wild-type poliovirus: 2 and 6, mock-transfected cells: 3 and 7, cells transfected with RNA derived from pT7-IC-GAG 1:4 and 8, cells transfected with RNA derived from pT7-IC-GAG 2; 5 and 9, cells transfected with RNA derived from pT7-IC-POL. The positions of molecular mass standards are indicated. A protein of molecular mass 72 kDa, corresponding to the 3CD protein of poliovirus, was immunoprecipitated by anti-$3D^{pol}$ antibodies from cells transfected with the recombinant poliovirus RNA but not from mock-transfected cells. Under the same conditions for metabolic labeling, the 3CD protein, which is a fusion protein between the $3C^{pol}$ and $3D^{pol}$ proteins of poliovirus, is predominantly detected upon incubation of lysates from poliovirus infected cells with $3D^{pol}$ antisera to determine whether the appropriate HIV-1-P1 fusion proteins were also expressed, the extracts were incubated with pooled AIDS patient sera (gag) or rabbit anti-RT antibodies (pol). Expression of the HIV-1-Gag-P1 fusion proteins corresponding to the predicted molecular masses 80 and 95 kDa were detected from cells transfected with RNA genomes derived by in vitro transcription of pT7-IC-GAG 1 and pT7-IC-GAG 2, respectively. Similarly, an HIV-1 Pol-P1 fusion protein of the predicted molecular mass 85 kDa was immunoprecipitated from cells transfected with RNA derived from the in vitro transcription of pT7-IC-POL. These results demonstrate that transfection of the recombinant poliovirus RNA into VV-P1 infected cells results in the expression of appropriate HIV-1-P1 fusion proteins as well as $3D^{pol}$ related proteins.

Encapsidation and serial passage of the chimeric HIV-1-poliovirus genomes with VV-P1

Figure 4A:
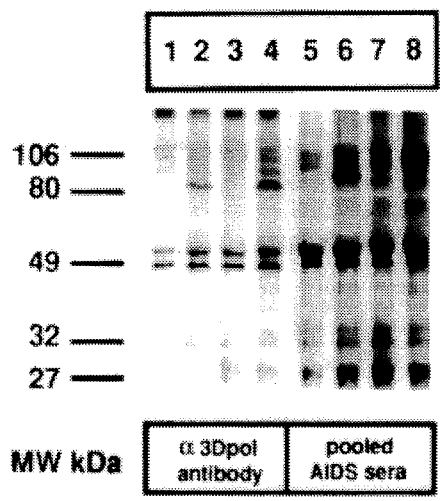
FIGS. 4A, 4B, and 4C show SDS-polyacrylamide gels on which poliovirus- and HIV-1-specific protein expression from cells infected with recombinant poliovirus RNA which were encapsidated and serially passaged with capsid proteins provided by VV-P1 were analyzed.
Figure 4B:
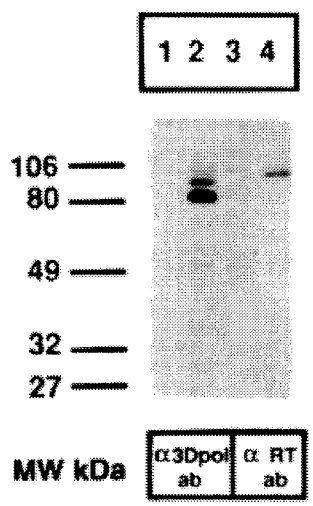

In order to determine whether transfection of the chimeric genomes into VV-P1 infected cells would result in encapsidation of the recombinant poliovirus nucleic acid, the recombinant poliovirus RNA's were transfected into either VV-P1 or wt VV-infected cells, and the encapsidation genomes were isolated as described in Materials and Methods. The pelleted material was then used to reinfect cells. This procedure was followed by metabolic labeling of viral proteins and incubation with anti-$3D^{pol}$ or HIV-1- antisera (FIGS. 4A and 4B). FIGS. 4A and 4B show an analysis of poliovirus- and HIV-1-specific protein expression from cells infected with recombinant poliovirus nucleic acids which were encapsidated and serially passaged with capsid proteins provided by VV-P1. Cells were infected with VV-P1 or wt VV at a multiplicity of infection of 20 and transfected with RNA derived from in vitro transcription of the designated plasmids. The cells were harvested for isolation of encapsidated genomes as described in Materials and Methods. The pelleted material was used to reinfect cells, which were metabolically labeled, and cell lysates were incubated with the designated antibodies. Immunoreactive proteins were analyzed on SDS-polyacrylamide gels. FIG. 4A: Lanes: 1 and 5, cells infected with pelleted material derived from cells infected with wt VV and transfected with RNA derived from pT7-IC-GAG 1; 2 and 6, cells infected with pelleted material derived from cells infected with VV-P1 and transfected with RNA derived from pT7-IC-GAG 1; 3 and 7, cells infected with pelleted material derived from cells infected with wt VV and transfected with RNA derived from pT7-IC-GAG 2; 4 and 8, cells infected with pelleted material derived from cells infected with VV-P1 and transfected with RNA derived from pT7-IC-GAG2. FIG. 4B: Lanes: 1 and 3, cells infected with pelleted material derived from cells infected with wt VV and transfected with RNA derived from pT7-IC-POL; 2 and 4, cells infected with pelleted material derived from cells infected with VV-P1 and transfected with RNA derived from PT7-IC-POL.

Figure 2A:
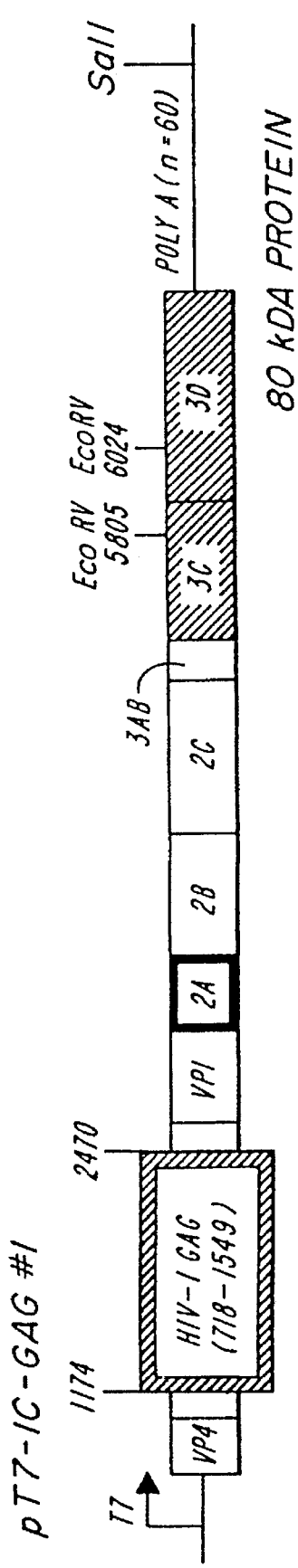
FIGS. 2A, 2B, and 2C show chimeric HIV-1-poliovirus genomes containing regions of the HIV-1 gag or pol gene substituted for the poliovirus P1 gene.
Figure 2B:
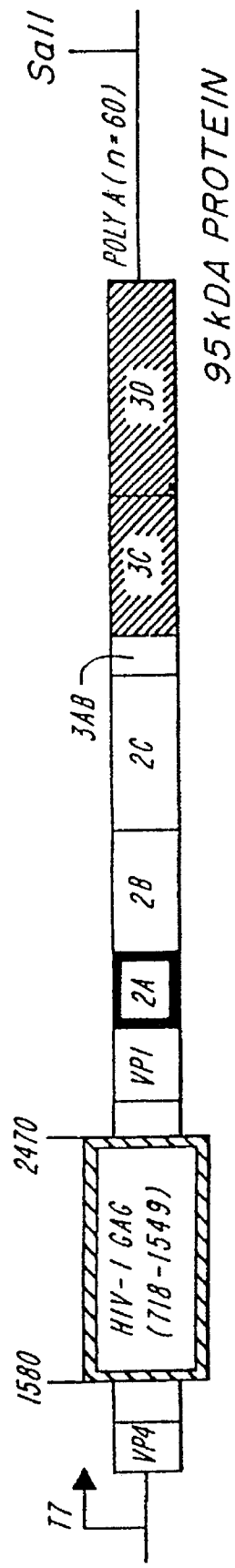
Figure 2C:
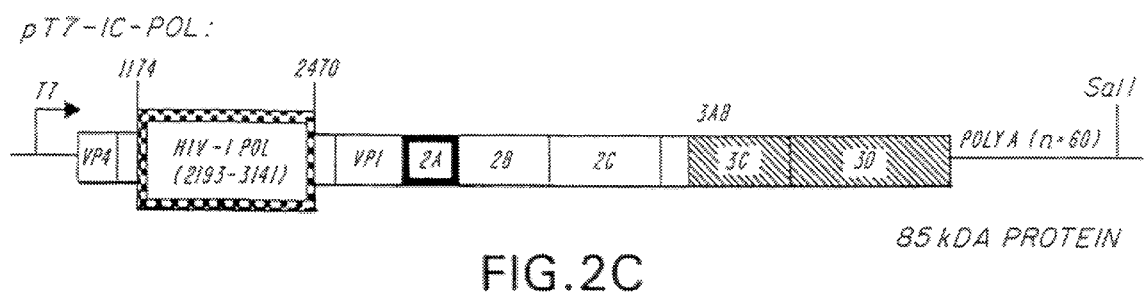

The poliovirus 3CD protein was immunoprecipitated from cells infected with pelleted material derived from transfection of the recombinant poliovirus RNA into VV-P1 infected cells. The molecular masses of the HIV-1-P1 fusion proteins immunoprecipitated from the infected cells were consistent with the predicted molecular masses and those observed from expression of the recombinant poliovirus nucleic acid in transfected cells (FIG. 2). No $3D^{pol}$ or HIV-1-P1 proteins were detected from cells infected with material derived from transfection of the chimeric genomes into wt VV-infected cells, demonstrating a requirement for the poliovirus P1 protein for encapsidation of the recombinant poliovirus nucleic acid.

Figure 4C:
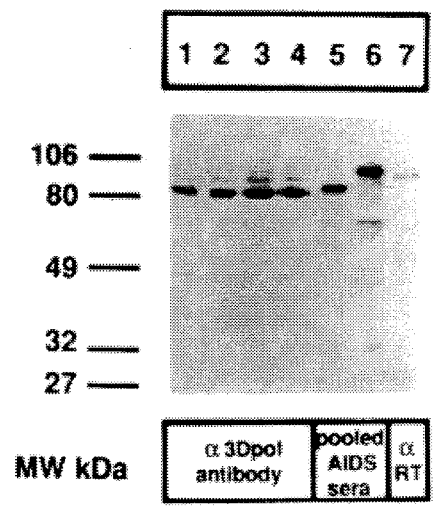

To determine whether the encapsidated recombinant poliovirus nucleic acid could be serially passaged, passage 1 stock of the encapsidated recombinant poliovirus nucleic acid was used to infect cells that had been previously infected with VV-P1. After 24 hours, the encapsidated recombinant poliovirus nucleic acids were isolated as described in Materials and Methods and subsequently used to reinfect cells which had been previously infected with VV-P1; this procedure was repeated for an additional nine passages. By convention the stocks of serially passaged recombinant poliovirus RNA are referred to as vIC-GAG 1, vIC-GAG 2, or vIC-POL. Cells were infected with passage 9 material and metabolically labeled and the lysates were incubated with antisera to poliovirus $3D^{pol}$ protein or antibodies to HIV-1 proteins (FIG. 4C). In FIG. 4C, stocks of the encapsidated recombinant poliovirus nucleic acids were also used to infect cells which had been previously infected with VV-P1 for serial passage of the encapsidated genomes as described in Materials and Methods. Cells were infected with serially passaged stocks of recombinant poliovirus nucleic acids at passage 9 and metabolically labeled, and cell extracts were incubated with the designated antibodies (ab). Immunoreactive proteins were analyzed on SDS-polyacrylamide gels. Lanes: 1, cells infected with wild-type poliovirus; 2 and 5, cells infected with vIC-GAG 1; 3 and 6, Cells infected with vIC-GAG2; 4 and 7, cells infected with vIC-POL. The positions of molecular mass standards are indicated.

Figure 3:
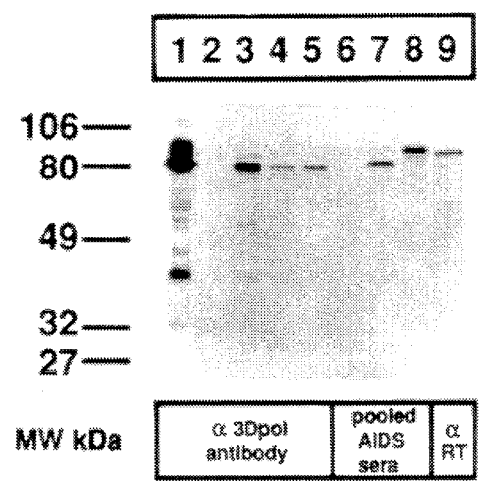
FIG. 3 shows an SDS-polyacrylamide gel on which $3D^{pol}$ and HIV-1-P1 fusion protein expression from cells infected with VV-P1 and transfected with recombinant poliovirus RNA was analyzed.

The poliovirus 3CD protein was immunoprecipitated from cells infected with poliovirus and the encapsidated recombinant poliovirus nucleic acids. The HIV-1-Gag-P1 and HIV-1-Pol-P1 fusion proteins were also immunoprecipitated from cells infected with the serially passaged recombinant poliovirus nucleic acids. In contrast, no immunoreactive proteins were detected from cells-which were infected with VV-P1 alone and immunoprecipitated with the same antisera (FIG. 3).

Figure 5:
FIG. 5 shows a Northern blot analysis of RNA isolated from a stock of encapsidated recombinant poliovirus nucleic acid.

To determine whether the encapsidated recombinant poliovirus nucleic acids had undergone any significant deletion of genome size as a result of serial passage with VV-P1, RNA isolated from vIC-GAG 1 at passage 14 was analyzed by Northern blotting (FIG. 5). FIG. 5 shows a Northern blot analysis of RNA isolated from a stock of encapsidated recombinant poliovirus nucleic acids. Virions were isolated by ultracentrifugation from a stock of vIC-GAG 1 at passage 14 and from type 1 Mahoney poliovirus. The isolated virions were disrupted, and the RNA was precipitated, separated in a formaldehyde-agarose gel, and transferred to nitrocellulose. Lanes: 1, RNA isolated from vIC-GAG 1 stock; 2, RNA isolated from poliovirions. Note that the exposure time for the sample in lane 1 of the gel was six times longer than that for lane 2.

For these studies, a riboprobe complementary to nucleotides 671 to 1174 of poliovirus, present in the HIV-1-poliovirus chimeric genomes, was used. RNA isolated from vIC-GAG 1 was compared with RNA isolated from type 1 Mahoney poliovirions. The migration of the RNA isolated from vIC-GAG 1 was slightly faster than that of the wild-type poliovirus RNA, consistent with the predicted 7.0-kb size for RNA from pT7-IC-GAG 1 versus the 7.5-kb size for wild-type poliovirus RNA. Furthermore, we detected a single predominant RNA species from vIC-GAG 1, indicating that no significant deletions of the RNA had occurred during the serial passages.

Antibody neutralization of recombinant poliovirus nucleic acid encapsidated by VV-P1

Figure 6:
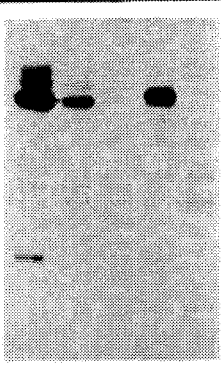
FIG. 6 shows an SDS-polyacrylamide gel on which the neutralization of the poliovirus nucleic acid encapsidated by VV-P1 with anti-poliovirus antibodies was analyzed.

To confirm that the recombinant poliovirus nucleic acid RNA passaged with VV-P1 was encapsidated in poliovirions, the capacity of poliovirus-specific antisera to prevent expression of the HIV-1-P1 fusion proteins and poliovirus 3CD protein was analyzed. The results of this experiment are important to exclude the possibility that the recombinant poliovirus nucleic acids were being passaged by inclusion into VV-P1 rather than poliovirions. For these studies, passage 9 material of vIC-GAG 1 was preincubated with preimmune type 1 poliovirus antisera as described in Materials and Methods. After incubation, the samples were used to infect cells, which were then metabolically labeled, and cell lysates were analyzed for expression of poliovirus- and HIV-1 specific proteins after incubation with anti-3D$^{pol}$ antisera and pooled AIDS patient sera, respectively (FIG. 6). FIG. 6 shows neutralization of recombinant poliovirus nucleic acids encapsidated by VV-P1 with anti-poliovirus antibodies. Cells were infected with a passage 9 stock of vIC-GAG 1 that had been preincubated with anti-poliovirus type 1 antisera or preimmune sera as described in Materials and Methods. Infected cells were metabolically labeled, cell lysates were incubated with anti-3D$^{pol}$ antibodies (lanes 1 to 3) or pooled AIDS patient sera (lanes 4 and 5), and immunoreactive proteins were analyzed on SDS-polyacrylamide gels. Lanes: 1, cells infected with wild-type poliovirus (no neutralization); 2 and 4, cells infected with vIC-GAG 1 which had been preincubated with preimmune sera: 3 and 5, cells infected with vIC-GAG 1 which had been preincubated with anti-poliovirus type 1 antisera. The positions of molecular mass standards are indicated.

No expression of the poliovirus 3CD or HIV-1-Gag-P1 fusion protein was detected from cells infected with vIC-GAG 1 which had been preincubated with the anti-poliovirus antibodies. Expression of 3CD protein and HIV-1-Gag-P1 fusion protein was readily detected from cells infected with vIC-GAG 1 which had been preincubated with normal rabbit serum (preimmune). These results demonstrate that the recombinant poliovirus nucleic acids were encapsidated by P1 protein provided in trans by VV-P1 which could be neutralized by anti-poliovirus antibodies.

Encapsidation of serially passaged recombinant poliovirus nucleic acids by poliovirus To determine whether the recombinant poliovirus nucleic acid genomes could be encapsidated by P1 protein provided in trans from wild-type poliovirus, cells were coinfected with type 1 Sabin poliovirus and passage 14 stock of vIC-GAG 1. Type 1 Sabin poliovirus was used for these studies because we were previously unable to encapsidate the recombinant poliovirus nucleic acids by transfection of chimeric RNA into cells infected with type 1 Mahoney which was derived from an infectious cDNA. In addition, a long-term goal of the studies is to evaluate the potential of recombinant poliovirus vaccines; therefore, encapsidation of the recombinant poliovirus nucleic acids with type 1 Sabin poliovirus would be an essential prerequisite for these studies. After 24 hours, the coinfected cells were harvested as described in Materials and Methods, and the extracted material was serially passaged 10 additional times at a high multiplicity of infection. Cells were infected with passage 10 material of vIC-GAG 1 and type 1 Sabin poliovirus and metabolically labeled, and cell extracts were incubated with antibodies to type 1 Sabine poliovirus (FIG. 7A), pooled sera from AIDS patients (FIG. 7B), and anti-p24 antibodies (FIG. 7C) and the immunoreactive proteins were analyzed on SDS polyacrylamide gels. Lanes: 1, cells infected with type 1 Sabin poliovirus alone; 2, cells infected with material derived from passage 10 of vIC-GAG 1 and type 1 Sabin poliovirus. The positions of relevant proteins are indicated.

Figure 7A:
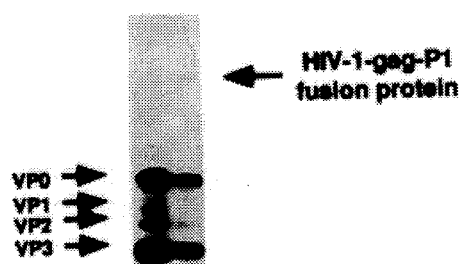
FIGS. 7A, 7B, and 7C show SDS-polyacrylamide gels on which poliovirus- and HIV-1-specific protein expression from cells infected with a stock of poliovirus nucleic acid encapsidated by type 1 Sabin poliovirus was analyzed.
Figure 7B:
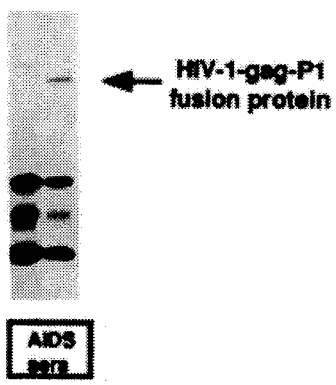
Figure 7C:
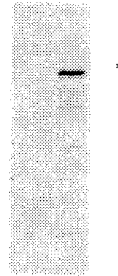

Poliovirus capsid proteins were detected from cells infected with type 1 Sabin poliovirus alone and from cells infected with material derived from passaging vIC-GAG 1 with type 1 Sabin poliovirus. No HIV-1 specific proteins were detected from cells infected with type 1 Sabin poliovirus alone. A slight cross-reactivity of the HIV-1-Gag-P1 fusion protein with anti-poliovirus antisera was detected in extracts of cells infected with material derived from passaging vIC-GAG 1 with type 1 Sabin poliovirus (FIG. 7A). Although the HIV-1-Gag-P1 fusion protein was clearly detected from cells with type 1 Sabin poliovirus after incubation with pooled AIDS patient sera, some cross-reactivity of the poliovirus capsid proteins were also detected (FIG. 7B). To confirm that we had immunoprecipitated the HIV-1-Gag p1 fusion protein from extracts of cells infected with material derived from passaging vIC-Gag 1 with type 1 Sabin poliovirus, we also incubated extracts with rabbit anti-p24 antiserum (FIG. 7C). Again, detection of the HIV-1-Gag-P1 fusion protein was evident from cells infected with material derived from passaging vIC-GAG1 with type 1 Sabin poliovirus but not from cells infected with type 1 Sabin alone. Furthermore, HIV-1-Gag-P1 fusion protein expression was detected after each serial passage (1 to 10) of vIC-GAG 1 with type 1 Sabin poliovirus. These results demonstrate that the chimeric recombinant poliovirus nucleic acids can be encapsidated by P1 protein provided in trans from type 1 Sabin poliovirus under the appropriate experimental conditions and are stable upon serial passage.

EXAMPLE 2

Immunization of mice with chimeric HIV-1 poliovirus nucleic acid

The construction and characterization of chimeric HIV-1 poliovirus nucleic acid in which the HIV-1 gag gene was substituted for VP2 and VP3 regions of the poliovirus P1 protein in the infectious cDNA of poliovirus was performed as described previously. Choi, W. S. et al. (1991)*J. Virol.* 65:2875–2883. To evaluate both qualitatively and quantitatively the immune responses against HIV-1 gag expressed from recombinant poliovirus nucleic acid, BALB/c mice (5 animals in each of three groups) were immunized by parenteral (intramuscular), oral (intragastric) or intrarectal routes. The doses were $2.5 \times 10^5$ virus pfu poliovirus/mouse for systemic immunization (intramuscular) and $2.5 \times 10^6$ pfu poliovirus/mouse for oral immunization. It is important to note that the titer refers only to the type II Lansing in the virus preparation, since the encapsidated recombinant poliovirus nucleic acid alone does not form plaques due to deletion of the P1 capsids. For oral immunization, the antigen was resuspended in 0.5 ml of RPMI 1640 and administered by means of an animal feeding tube (see Moldoveanu et al. (1993) *J. Infect. Dis.* 167:84–90). Intrarectal immunization was accomplished by application of a small dose of virus in solution (10 µl/mouse intrarectally). Serum, saliva, fetal extract and vaginal lavage were collected before immunization, and two weeks after the initial dose of the virus.

Collection of Biological Fluids

Biological fluids were collected two weeks after the primary immunization, and one week after the secondary immunization. The methods for obtaining biological fluids are as follows:

Blood was collected from the tail vein with heparinized glass capillary tubes before and at selected times after immunization. The blood was centrifuged and plasma collected and stored at −70° C.

Stimulated saliva was collected with capillary tubes after injection with carbamylcholine (1–2 µg/mouse). Two µg each of soybean trypsin inhibitor and phenylmethylsulfonyl fluoride (PMSF) was added to the sample followed by clarification by centrifugation at 800×g for 15 minutes. Sodium azide (0.1% final concentration) and FCS (1% final concentration) was added after clarification and the sample stored at −70° C. until the assay.

Vaginal lavages were performed in mice by applying approximately 50 μl sterile PBS into the vagina and then aspirating the outcoming fluid.

Intestinal lavages were performed according to the methods previously described by Elson et al. (Elson, C. O. et al. (1984) *J. Immunol. Meth.* 67:101–108). For those studies, four doses of 0.5 ml lavage solution (isoosmotic for mouse gastrointestinal secretion) was administered at 15 minute intervals using an intubation needle. Fifteen minutes after the last dose of lavage, 0.1 μg of polycarbine was administered by intraperitoneal injection to the anesthetized mouse. Over the next 10 to 15 minutes the discharge of intestinal contents was collected into a petri dish containing a 5 ml solution of 0.1 mg/ml trypsin soybean inhibitor and 5 mM EDTA. The solid material was removed by centrifugation (650×g for 10 minutes at 4° C.) and the supernatant collected. Thirty μl of 100 mM PMSF was then added followed by further clarification at 27,000×g for 20 minutes at 4° C. An aliquot of 10 μl of 0.1% sodium azide and 10% fetal calf serum was added before storage at −70° C.

Fecal Extract was prepared as previously described (Keller, R., and Dwyer, J. E. (1968)*J. Immunol.* 101: 192–202).

Analysis of the Anti-Poliovirus and HIV-1 gag Antibodies Enzyme-Linked Immunoabsorbant Assay An ELISA was used for determining antigen-specific antibodies as well as for total levels of immunoglobulins. The assay was performed in 96-well polystyrene microtiter plates (Dynatech, Alexandria, Va.). For coating, purified poliovirus (1 μg/well) or HIV specific proteins, or solid phase adsorbed, and affinity-purified polyclonal goat IgG antibodies specific for mouse IgG, IgA or IgM (Southern Biotechnology Associates, Birmingham, Ala. (SBA)(1 μg/well)) were employed. Dilutions of serum or secretions were incubated overnight at 4° C. on the coated and blocked ELISA plates and the bound immunoglobulins were detected with horseradish peroxidase-labeled goat IgG against mouse Ig, IgA, IgG, or IgM (SBA). At the end of the incubation time (3 hours at 37° C.), the peroxidase substrate 2,2-azino bis. (3-ethylbenzthiazoline) sulfonic acid (ABTS) (Sigma, St. Louis, Mo.) in citrate buffer pH 4.2 containing 0.0075% $H_2O_2$ was added. The color developed was measured in a Titertek Multiscan photometer (Molecular Devices, Palo Alto, Calif.) at 414 nm. To calibrate the total level of mouse IgA, IgG, IgM levels, purified mouse myeloma proteins available in our laboratory served as standards. For antigen-specific ELISA, the optical densities were converted to ELISA units, using calibration curves obtained from optical density values obtained from reference pools of sera or secretions. The calibration curves were constructed using a computer program on either 4-parameter logistic or weighed logit-log models. End point titration values were an alternative way of expressing the results. The fold increase values were calculated by dividing post-immunization by pre-immunization values expressed in ELISA units.

Figure 8A:
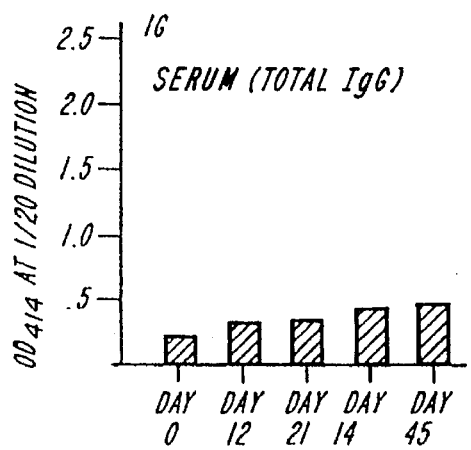
FIGS. 8A, 8B, and 8C show total anti-poliovirus IgG levels in serum from mice after intragastric, intrarectal, and intramuscular administration of an encapsidated recombinant poliovirus nucleic acid encoding and expressing at least a portion of the gag protein of human immunodeficiency virus type 1.
Figure 8B:
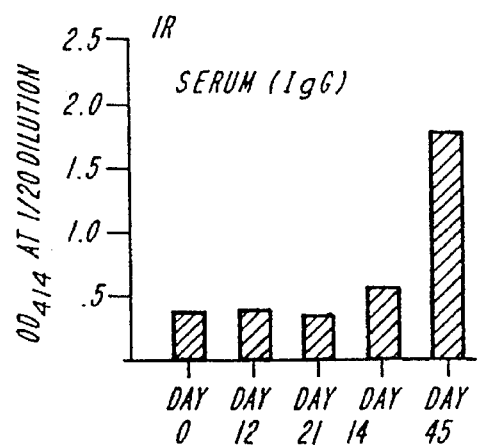
Figure 8C:
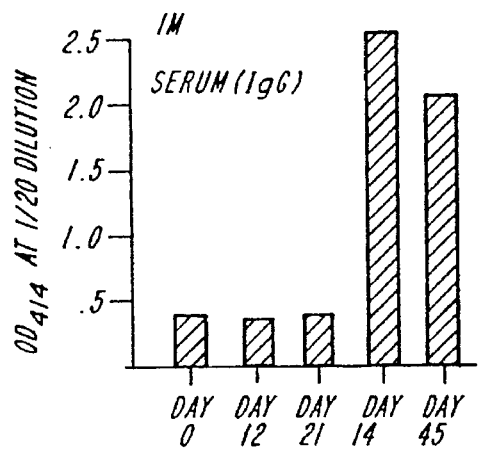

Anti-poliovirus or anti-gag antibodies in mice immunized with encapsidated recombinant poliovirus nucleic acid Anti-poliovirus antibodies The levels of anti-poliovirus antibodies were determined by ELISA at Day 0 (pre-immune), Days 12, and 21 post immunization. A second administration of encapsidated recombinant poliovirus nucleic acid was given by the same route at day 21, and samples were collected 14 days post to second booster and 45 days post second booster. FIGS. 8A, 8B, and 8C show serum anti-poliovirus antibodies (designated total IgG, representing predominantly IgG, with minor contribution of IgM and IgA) for animals immunized via the intragastric, intrarectal, or intramuscular route. The samples from each of the 5 animals within the group were pooled, and the ELISA was used to determine the amounts of anti-poliovirus antibodies at a 1:20 dilution. A very slight increase in the anti-poliovirus antibodies present in the serum of mice immunized via the intragastric route was observed at Day 45 post booster immunization when compared to the pre-immune levels at Day 0. A clear increase in the serum anti-poliovirus antibodies was observed in the animals immunized via the intragastric or intramuscular route at Day 14 and Day 45 post booster immunization. The levels at Day 14 and 45 post booster immunization were approximately 5-fold over that observed for the background levels at Day 0.

Figure 9A:
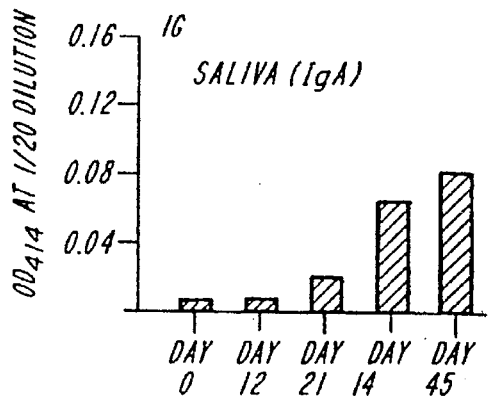
FIGS. 9A, 9B, and 9C show anti-poliovirus IgA levels in saliva from mice after intragastric, intrarectal, and intramuscular administration of an encapsidated recombinant poliovirus nucleic acid encoding and expressing at least a portion of the gag protein of human immunodeficiency virus type 1.
Figure 9B:
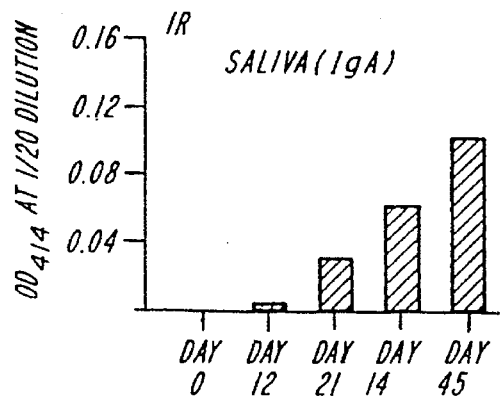
Figure 9C:
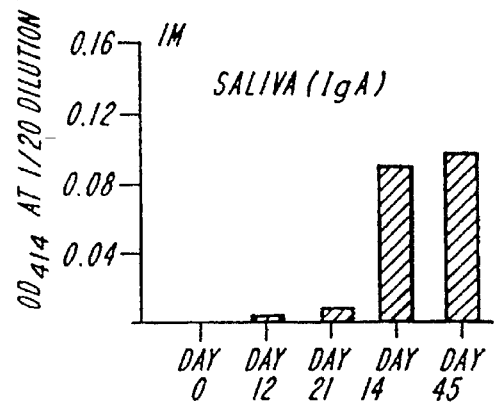
Figure 10A:
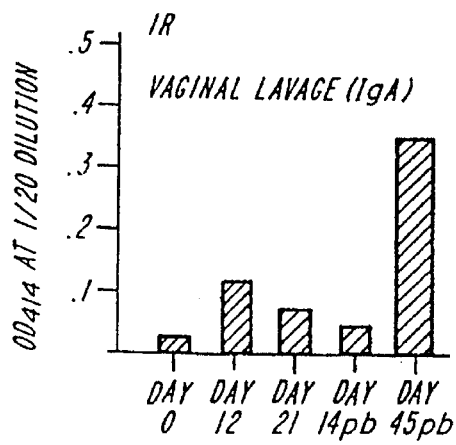
FIGS. 10A and 10B show anti-poliovirus IgA in vaginal lavages after intrarectal, and intramuscular administration of an encapsidated recombinant poliovirus nucleic acid encoding and expressing at least a portion of the gag protein of human immunodeficiency virus type 1.
Figure 10B:
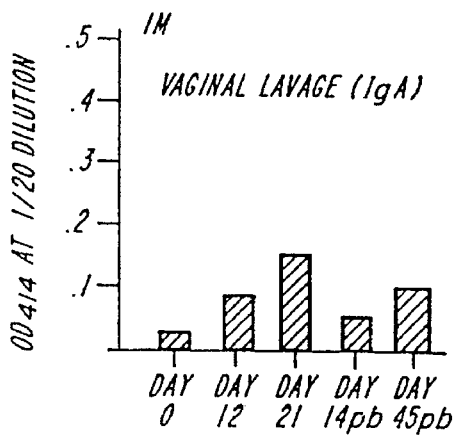
Figure 11A:
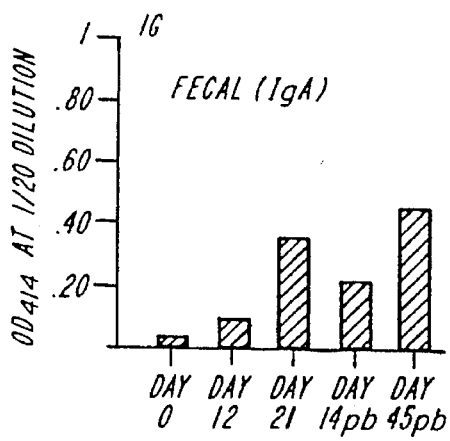
FIGS. 11A, 11B, and 11C show anti-poliovirus IgA in feces from mice after intragastric, intrarectal, and intramuscular administration of an encapsidated recombinant poliovirus nucleic acid encoding and expressing at least a portion of the gag protein of human immunodeficiency virus type 1.
Figure 11B:
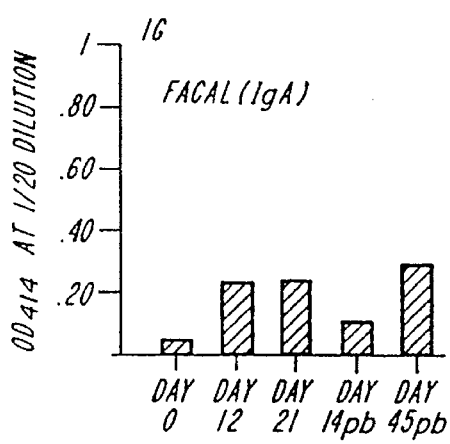
Figure 11C:
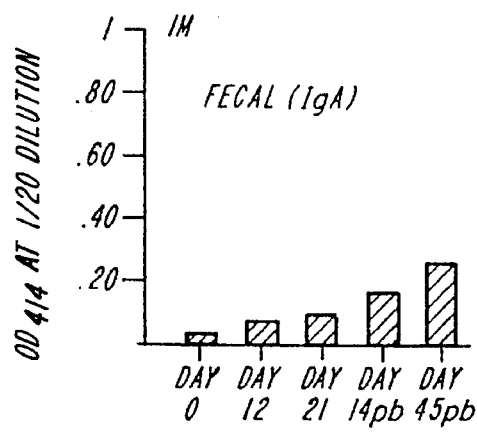

In FIGS. 9A, 9B, and 9C, IgA anti-poliovirus antibodies present in the saliva of animals immunized with the encapsidated recombinant poliovirus nucleic acids were analyzed. In this case, there was a clear increase in the levels of IgA anti-poliovirus antibodies in animals immunized via the intragastric, intrarectal, or intramuscular route at Day 14 and 45 post booster immunization. In FIGS. 10A and 10B, IgA anti-poliovirus antibodies from the vaginal lavage samples taken from mice immunized via the intrarectal or intramuscular route were analyzed. In this case, there was a clear increase over the preimmune values at Day 45 post booster immunization with animals immunized via the intrarectal route. In contrast, there was not a significant increase in the levels of IgA anti-poliovirus antibodies in animals immunized via the intramuscular route. Finally, as shown in FIGS. 11A, 11B, and 11C, IgA anti-poliovirus antibodies were present in extracts from feces obtained from animals immunized via the intragastric, intrarectal or intramuscular route. In all cases, there was an increase of the IgA anti-poliovirus antibodies at Day 21, Day 14 post booster immunization and Day 45 post booster immunization. Levels were approximately 5-fold over the pre-immune levels taken at Day 0. It is possible that the levels of anti-poliovirus detected have been underestimated due to the possibility that the animals are also shedding poliovirus in the feces at this time. The shed poliovirus as well as anti-poliovirus antibodies form an immune complex which would not be detected in the ELISA assay.

Anti-HIV-1-gag Antibodies

Figure 12A:
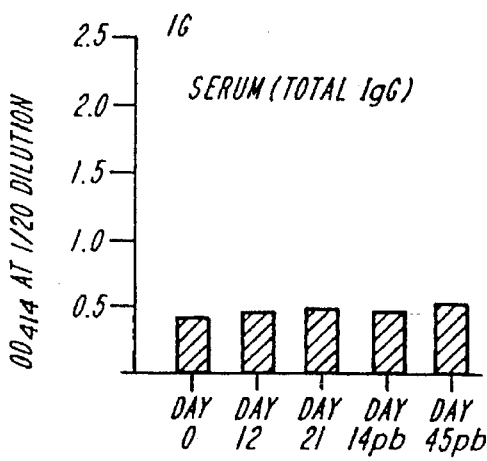
FIGS. 12A, 12B, and 12C show anti-HIV-1-Gag IgG in serum from mice after intragastric, intrarectal, and intramuscular administration of an encapsidated recombinant poliovirus nucleic acid encoding and expressing at least a portion of the gag protein of human immunodeficiency virus type 1.
Figure 12B:
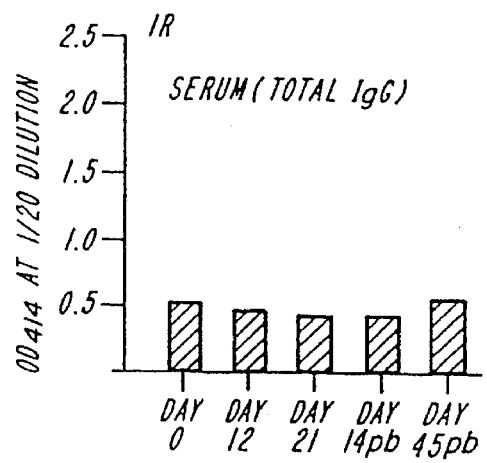
Figure 12C:
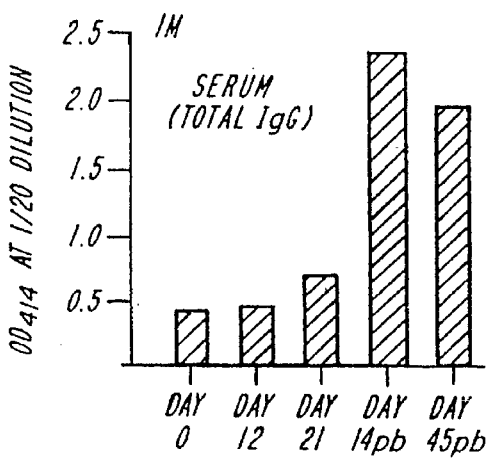

Portions of the same samples that were collected to analyze anti-poliovirus antibodies were analyzed for the presence of anti-HIV-1-gag-antibodies. FIGS. 12A, 12B, and 12C show the serum levels of total IgG (representing IgG as the major species and IgM and IgA as the minor species) anti-HIV-1-gag antibodies in the serum of animals immunized via the intragastric, intrarectal, or intramuscular route. No consistent increase in the levels of serum antibodies directed against HIV-1-gag antibodies in animals immunized via the intragastric or intrarectal route was observed. This is represented by the fact that there was no increase in the levels above that observed at Day 0 (pre-immune) value. In contrast, there was an increase in the anti-HIV-1-gag antibodies levels in mice immunized via the intramuscular route. On Day 21 post immunization, there was a clear increase over the background value. The levels of anti-HIV-1-gag antibodies in the serum at Days 14 post boost and 45 post boost were clearly above the pre-immune values in the animals immunized via the intramuscular route.

Figure 13A:
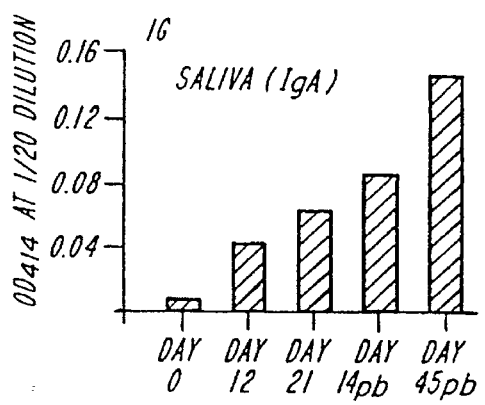
FIGS. 13A, 13B, and 13C show anti-HIV-1-Gag IgA in saliva from mice after intragastric, intrarectal, and intramuscular administration of an encapsidated recombinant poliovirus nucleic acid encoding and expressing at least a portion of the gag protein of human immunodeficiency virus type 1.
Figure 13B:
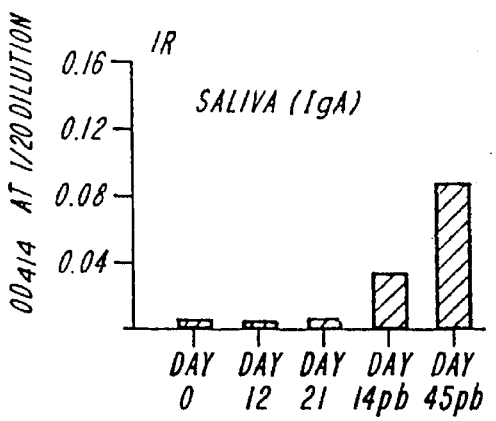
Figure 13C:
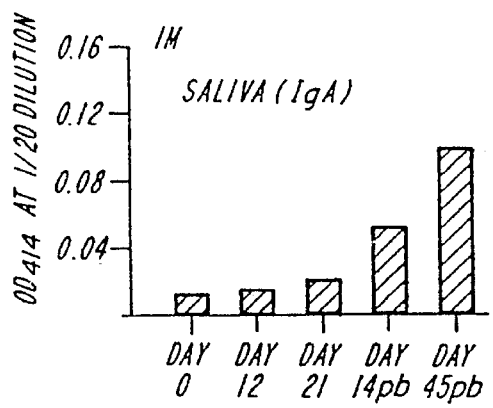
Figure 14A:
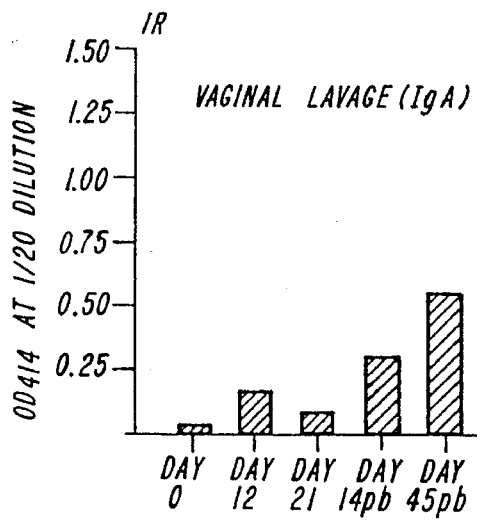
FIGS. 14A and 14B show anti-HIV-1-Gag IgA in vaginal lavages from mice after intragastric, intrarectal, and intramuscular administration of an encapsidated recombinant poliovirus nucleic acid encoding and expressing at least a portion of the gag protein of human immunodeficiency virus type 1.
Figure 14B:
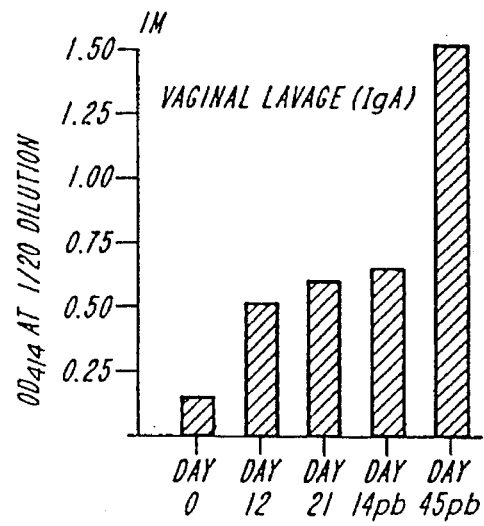
Figure 15A:
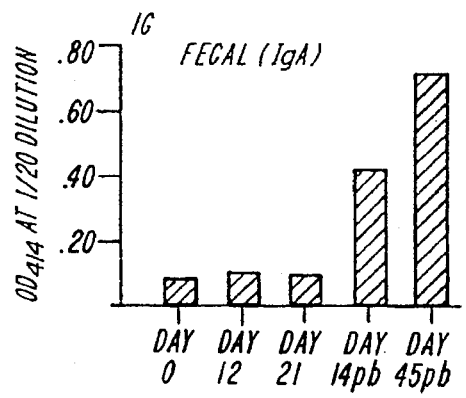
FIGS. 15A, 15B, and 15C show anti-HIV-1-Gag IgA in feces from mice after intragastric, intrarectal, and intramuscular administration of an encapsidated recombinant poliovirus nucleic acid encoding and expressing at least a portion of the gag protein of human immunodeficiency virus type 1.
Figure 15B:
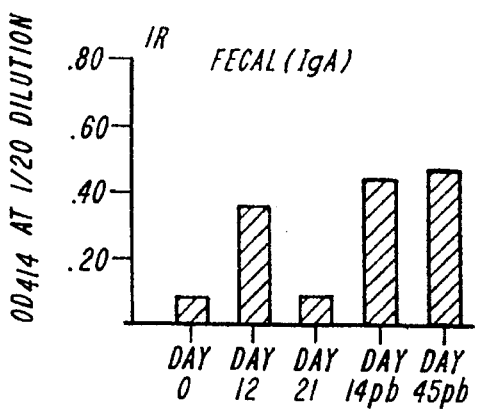
Figure 15C:
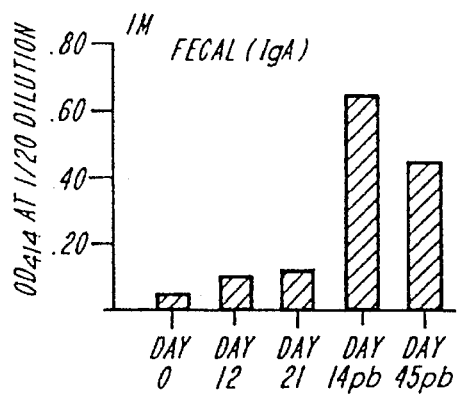
Figure 16:
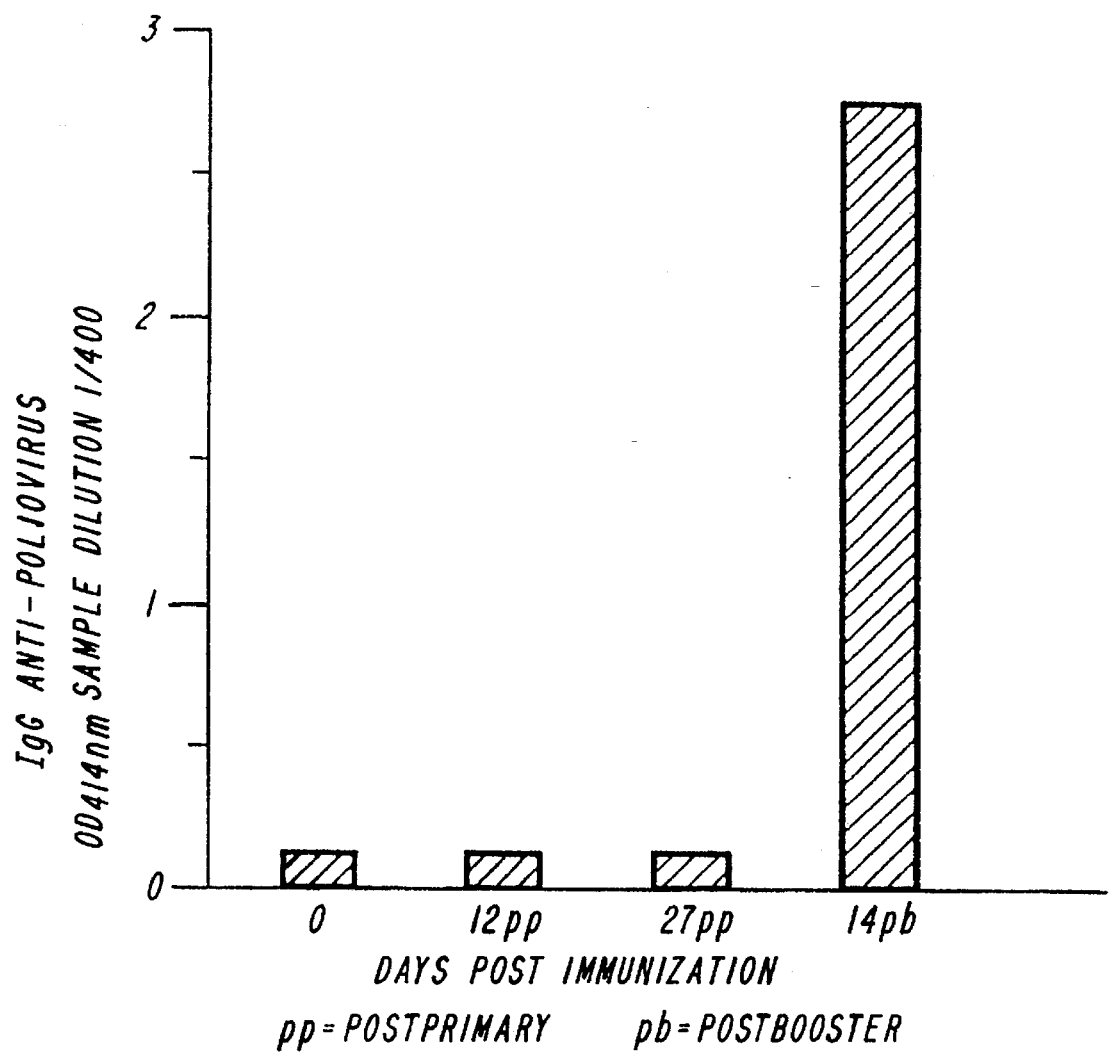
FIG. 16 shows anti-poliovirus IgG from serum of a pigtail macaque after intrarectal administration of an encapsidated recombinant poliovirus nucleic acid encoding and expressing at least a portion of the gag protein of human immunodeficiency virus type 1.

In FIGS. 13A, 13B, and 13C, IgA anti-HIV-1-gag antibodies present in the saliva of animals immunized via the intragastric, intrarectal or intramuscular route. In this case, there was a clear increase over the pre-immune levels (Day 0) in animals immunized by all three routes of immunization. The highest levels of IgA anti-HIV-1-gag antibodies in the saliva were found at Day 45 post booster immunization. FIGS. 14A and 14B show a similar pattern for the samples obtained from vaginal lavage of animals immunized via the intrarectal or intramuscular route. In this instance, there was a clear increase at Days 14 and 45 post booster immunization in the levels of IgA anti-HIV-1-gag antibodies from animals immunized via the intrarectal route of immunization. The animals immunized via the intramuscular route exhibited an increase of IgA anti-HIV-1-gag antibodies in vaginal lavage samples starting at Day 12 through Day 21. The levels increased following the booster immunization at Day 21 resulting in the highest levels observed at Day 45 post booster immunization. In FIGS. 15A, 15B, and 15C, IgA anti-HIV-1-gag antibodies present in fecal extracts obtained from animals immunized via the three different routes were analyzed. In general, there was an increase of the pre-immune levels using all three routes of immunization that was most evident at Days 14 and 45 post booster immunization. The results of these studies clearly establish that administration of the encapsidated recombinant HIV-1-poliovirus nucleic acids via the intragastric, intrarectal, or intramuscular route results in the generation of anti-HIV-1-gag antibodies in serum, saliva, vaginal lavage, as well as fecal extracts. A greater serum anti-HIV-1-gag antibody response was obtained by immunization of the animals via the intramuscular route rather than the intragastric or intrarectal routes. However, IgA anti-HIV-1-gag antibodies in secretions of animal immunized via all three routes were observed.

EXAMPLE 3

A pigtail macaque was immunized with $5\times10^8$ pfu of a virus stock of type I attenuated poliovirus containing the encapsidated recombinant nucleic acid from pT7IC-Gag #2 (FIG. 2 ). For these studies, intrarectal immunization was performed because of the high concentration of gut associated lymphoid tissue in the rectum of primates. The virus was deposited in a volume of 1 ml using a syringe filter with soft plastic tubing and inserted 1 inch into the rectum. The analysis of the anti-poliovirus and anti-gag antibodies was as described in Example 2 except that anti-monkey-specific reagents were substituted for anti-murine-specific reagents.

Serum from the macaque prior to immunization (Day 0), 12 days post primary immunization (12pp), 27 days post primary immunization (27pp) were collected. A second administration of virus consisting of 1 ml of $5\times10^8$ pfu given intrarectally and $2.5\times10^7$ pfu of virus administered intranasally at 27 days post primary immunization. Fourteen days after the second administration of virus (14 days post booster) serum was collected.

All serum samples were diluted 1:400 in PBS and the levels of IgG anti-poliovirus antibody were determined by ELI SA as described above. As shown in FIG. 16, there was a clear increase in the serum IgG anti-poliovirus antibodies, as measured by $OD_{414}$ in the ELISA, in the immunized macaque at 14 days post booster immunization. The levels were approximately 10-fold higher than the previous levels (Day 0). This study shows that intrarectal primary followed by intrarectal-intranasal booster immunization results in clear increase in the IgG anti-poliovirus antibodies.

Equivalents

Those skilled in the art will recognize, or be able to ascertain using no more than routine experimentation, many equivalents to the specific embodiments of the invention described herein. Such equivalents are intended to be encompassed by the following claims.

All referenced patents and publications are hereby incorporated by reference in their entirety.

I claim:

1. A method for encapsidating a recombinant poliovirus nucleic acid, comprising the steps of:
   (a) providing a recombinant poliovirus nucleic acid which lacks a nucleotide sequence encoding at least a portion of a protein necessary for encapsidating the recombinant poliovirus nucleic acid such that the recombinant poliovirus nucleic acid does not express proteins sufficient for encapsidation and an expression vector lacking an infectious poliovirus genome, the nucleic acid of which encodes at least a portion of a protein necessary for encapsidating the recombinant poliovirus nucleic acid and directs expression of at least a portion of a protein necessary for encapsidating the recombinant poliovirus nucleic acid; and
   (b) contacting a host cell with the recombinant poliovirus nucleic acid and the expression vector under conditions, appropriate for introduction of the recombinant poliovirus nucleic acid and the expression vector into the host cell; and
   (c) obtaining a yield of encapsidated viruses which substantially comprises encapsidated recombinant poliovirus nucleic acid.

2. The method of claim 1 wherein the expression vector is introduced into the host cell prior to the introduction of the recombinant poliovirus nucleic acid.

3. The method of claim 1 wherein the recombinant poliovirus nucleic acid is derived from a poliovirus serotype selected from the group consisting of poliovirus type I, poliovirus type II, and poliovirus type III.

4. The method of claim 1 wherein the nucleotide sequence encoding at least a portion of a protein necessary for encapsidating the recombinant poliovirus nucleic acid which the recombinant poliovirus nucleic acid lacks is replaced by a foreign nucleotide sequence encoding, in an expressible form, a foreign protein or fragment thereof.

5. The method of claim 1 wherein the expression vector comprises a virus.

6. The method of claim 5 wherein the virus is a recombinant vaccinia virus.

7. The method of claim 6 wherein the nucleic acid of the recombinant vaccinia virus encodes the poliovirus capsid precursor protein P1 and directs expression of a nucleotide sequence coding for the poliovirus capsid precursor protein P1.

8. The method of claim 1 wherein the expression vector comprises a plasmid.

9. The method of claim 8 wherein the nucleic acid of the plasmid encodes the poliovirus capsid precursor protein P1 and directs expression of a nucleotide sequence coding for poliovirus capsid precursor protein P1.

10. The method of claim 4 wherein the nucleotide sequence encoding at least a portion of a protein necessary for encapsidating the recombinant poliovirus nucleic acid which the recombinant poliovirus nucleic acid lacks comprises the VP2 and VP3 genes of the P1 capside precursor region.

11. The method of claim 10 wherein the foreign nucleotide sequence is selected from the group consisting of at least a portion of the gag gene, the pol gene, and the env gene of human immunodeficiency virus type 1.

12. The method of claim 11 wherein the foreign nucleotide sequence comprises at least a portion of the gag gene of human immunodeficiency virus type 1 (SEQ ID NO: 3).

13. The method of claim 11 wherein the foreign nucleotide sequence comprises at least a portion of the pol gene of human immunodeficiency virus type 1 (SEQ ID NO: 5).

14. The method of claim 11 wherein the foreign nucleotide sequence comprises at least a portion of the env gene of human immunodeficiency virus type 1 (SEQ ID NO: 7).

15. The method of claim 1 wherein the host cell is a mammalian host cell.

16. A method for serially passaging an encapsidated recombinant poliovirus nucleic acid, comprising the steps of:
  (a) providing a recombinant poliovirus nucleic acid having a foreign nucleotide sequence substituted for the nucleotide sequence which encodes at least a portion of a protein necessary for encapsidating the recombinant poliovirus nucleic acid and a viral expression vector lacking an infectious poliovirus genome, the nucleic acid of which encodes at least a portion of a protein necessary for encapsidating the recombinant poliovirus nucleic acid;
  (b) contacting a first host cell with the encapsidated recombinant poliovirus nucleic acid and the viral expression vector under conditions appropriate for introduction of the viral expression vector and the recombinant poliovirus nucleic acid into the host cell and for production of the encapsidated recombinant poliovirus nucleic acid and the viral expression vector by the host cell; and
  (c) infecting a second host cell with the encapsidated recombinant poliovirus and the viral expression vector produced by the first host cell.

17. A method for encapsidating a recombinant poliovirus nucleic acid, comprising the steps of:
  (a) providing a recombinant poliovirus nucleic acid which lacks the nucleotide sequence coding for the VP2 and VP3 genes of the P1 capsid precursor region and providing a recombinant vaccinia virus, the nucleic acid of which encodes the poliovirus capsid precursor protein P1 and directs expression of the poliovirus capsid precursor protein P1;
  (b) contacting a mammalian host cell with the recombinant poliovirus nucleic acid and the recombinant vaccinia virus under conditions appropriate for introduction of the recombinant poliovirus nucleic acid and the recombinant vaccinia virus into the mammalian host cell; and
  (c) obtaining a yield of encapsidated viruses which substantially comprises encapsidated recombinant poliovirus nucleic acid.

18. The method of claim 17 wherein the nucleotide sequence of the recombinant poliovirus nucleic acid which encodes the VP2 and VP3 genes of the P1 capsid precursor region is replaced by a foreign nucleotide sequence encoding, in an expressible form, a foreign protein or fragment thereof.

19. The method of claim 18 wherein the foreign nucleotide sequence is selected from the group consisting of at least a portion of the gag gene, the pol gene, and the env gene of human immunodeficiency virus type 1.

20. The method of claim 19 wherein the foreign nucleotide sequence comprises at least a portion of the gag gene of human immunodeficiency virus type 1(SEQ ID NO:3).

21. The method of claim 13 wherein the foreign nucleotide sequence comprises at least a portion of the pol gene of human immunodeficiency virus type 1 (SEQ ID NO: 5).

22. The method of claim 19 wherein the foreign nucleotide sequence comprises at least a portion of the env gene of human immunodeficiency virus type 1 (SEQ ID NO: 7).

23. An encapsidated recombinant poliovirus nucleic acid produced by the method of claim 1.

24. An encapsidated recombinant poliovirus nucleic acid produced by the method of claim 17.

25. An immunogenic composition, comprising:
  an encapsidated recombinant poliovirus nucleic acid and a physiologically acceptable carrier wherein at least a portion of a capsid protein of the encapsidated recombinant poliovirus nucleic acid is encoded and expressed by an expression vector which lacks an infectious poliovirus genome, the encapsidated recombinant poliovirus nucleic acid further having a foreign nucleotide sequence substituted for a poliovirus nucleotide sequence which encodes at least a portion of a protein necessary for encapsidating the recombinant poliovirus nucleic acid, the foreign nucleotide sequence encoding, in an expressible form, an immunogenic protein or fragment thereof.

26. The composition of claim 25 wherein the immunogenic protein or fragment thereof is a human immunodeficiency virus type 1 protein.

27. The composition of claim 26 wherein the human immunodeficiency virus type 1 protein is selected from the group consisting of at least a portion of the human immunodeficiency virus type 1 gag protein, the human immunodeficiency virus type 1 pol protein, and the human immunodeficiency virus type 1 env protein.

28. The composition of claim 27 wherein the human immunodeficiency virus type 1 protein comprises at least a portion of the human immunodeficiency virus type 1 gag protein (SEQ ID NO: 4).

29. The composition of claim 27 wherein the human immunodeficiency virus type 1 protein comprises at least a portion of the human immunodeficiency virus type 1 pol protein (SEQ ID NO: 6).

30. The composition of claim 27 wherein the human immunodeficiency virus type 1 protein comprises at least a portion of the human immunodeficiency virus type 1 env protein (SEQ ID NO:8).

31. A method for generating cells that produce a foreign protein or portion thereof, comprising the steps of:
  (a) contacting cultured host cells with
    (i) a recombinant poliovirus nucleic acid having a foreign nucleotide sequence substituted for the nucleotide sequence which encodes at least a portion of a protein necessary for encapsidating the recombinant poliovirus nucleic acid; and
    (ii) an expression vector lacking an infectious poliovirus genome, the nucleic acid of which encodes at least a portion of a protein necessary for encapsidation of the recombinant poliovirus nucleic acid and directs expression of at least a portion of a protein necessary for encapsidating the recombinant poliovirus nucleic acid; and
  (b) maintaining the cultured host cells under conditions appropriate for introduction of the recombinant poliovirus nucleic acid and the expression vector into the host cells, thereby generating modified cells which produce a foreign protein or fragment thereof.

32. An encapsidated recombinant poliovirus nucleic acid which lacks a nucleotide sequence encoding at least a portion of a protein necessary for encapsidating the recombinant poliovirus nucleic acid such that the encapsidated recombinant poliovirus nucleic acid does not express proteins sufficient for encapsidation, the encapsidated recombinant poliovirus nucleic acid being substantially free of a nucleic acid comprising the nucleotide sequence which is lacking in the encapsidated recombinant poliovirus nucleic acid.

33. The encapsidated recombinant poliovirus nucleic acid of claim 32, which is ribonucleic acid.

34. The encapsidated recombinant poliovirus nucleic acid of claim 32, which is selected from the group consisting of poliovirus type I, poliovirus type II, and poliovirus type III.

35. The encapsidated recombinant poliovirus nucleic acid of claim 32, which lacks the nucleotide sequence encoding at least a portion of the capsid precursor protein P1.

36. The encapsidated recombinant poliovirus nucleic acid of claim 35, which lacks the nucleotide sequence encoding at least a portion of the capsid proteins VP1 and VP2, VP1 and VP3, VP1 and VP4, VP2 and VP3, VP2 and VP4, or VP3 and VP4.

37. The encapsidated recombinant poliovirus nucleic acid of claim 35, which lacks the nucleotide sequence encoding the entire capside precursor protein P1.

38. The encapsidated recombinant poliovirus nucleic acid of claim 32, wherein the nucleotide sequence which the encapsidated recombinant poliovirus nucleic acid lacks is replaced by a foreign nucleotide sequence encoding, in an expressible form, a foreign protein or fragment thereof.

39. The encapsidated recombinant poliovirus nucleic acid of claim 38, wherein the foreign nucleotide sequence encodes a protein or fragment thereof selected from the group consisting of a viral antigen or fragment thereof, a bacterial antigen or fragment thereof, a tumor antigen or fragment thereof, an immunological response modifier or fragment thereof, and a protein with enzymatic activity or fragment thereof.

40. The encapsidated recombinant poliovirus nucleic acid of claim 39, wherein the viral antigen or fragment thereof is an HIV antigen or fragment thereof.

41. The encapsidated recombinant poliovirus nucleic acid of claim 40, wherein the HIV antigen is selected from the group consisting of the gag protein or a fragment thereof, the pol protein or a fragment thereof, and the env protein or a fragment thereof.

42. An encapsidated recombinant poliovirus nucleic acid which lacks a nucleotide sequence encoding at least a portion of a protein necessary for encapsidating the recombinant poliovirus nucleic acid such that the encapsidated recombinant poliovirus nucleic acid does not express proteins sufficient for encapsidation, the encapsidated recombinant poliovirus nucleic acid being substantially free of an encapsidated poliovirus nucleic acid comprising the nucleotide sequence which is lacking in the encapsidated recombinant poliovirus nucleic acid.

43. The encapsidated recombinant poliovirus nucleic acid of claim 42, wherein the nucleotide sequence encoding at least a portion of a protein necessary for encapsulating the recombinant poliovirus nucleic acid which the encapsulated recombinant poliovirus nucleic acid lacks is replaced by a foreign nucleotide sequence encoding, in an expressible form, a foreign protein or fragment thereof.

44. An encapsidated recombinant poliovirus nucleic acid which lacks a nucleotide sequence encoding at least a portion of a protein necessary for encapsidating the recombinant poliovirus nucleic acid such that the encapsidated recombinant poliovirus nucleic acid does not express proteins sufficient for encapsidation, the encapsidated recombinant poliovirus nucleic acid being substantially free of a vector comprising an infectious poliovirus genome.

45. The encapsidated recombinant poliovirus nucleic acid of claim 44, wherein the nucleotide sequence encoding at least a portion of a protein necessary for encapsidating the recombinant poliovirus nucleic acid which the encapsidated recombinant poliovirus nucleic acid lacks is replaced by a foreign nucleotide sequence encoding, in an expressible form, a foreign protein or fragment thereof.

46. A recombinant poliovirus nucleic acid wherein the nucleotide sequence encoding the entire P1 capsid precursor region of the poliovirus genome is replaced with a foreign nucleotide sequence.

47. The recombinant poliovirus nucleic acid of claim 46, which is ribonucleic acid.

48. A recombinant poliovirus nucleic acid wherein the nucleotide sequence encoding at least a portion of the capsid proteins VP1 and VP2, VP1 and VP3, or VP1 and VP4 is replaced with a foreign nucleotide sequence.

49. A method for encapsidating a recombinant poliovirus nucleic acid, comprising the steps of:
  (a) providing a recombinant poliovirus nucleic acid which lacks a nucleotide sequence encoding at least a portion of a capsid protein and an expression vector lacking an infectious poliovirus genome, the nucleic acid of which encodes at least a portion of a capsid protein and directs expression of at least a portion of a capsid protein; and
  (b) contacting a host cell with the recombinant poliovirus nucleic acid and the expression vector under conditions appropriate for introduction of the recombinant poliovirus nucleic acid and the expression vector into the host cell; and
  (c) obtaining a yield of encapsidated viruses which substantially comprises encapsidated recombinant poliovirus nucleic acid.

50. A method for encapsidating a recombinant poliovirus nucleic acid, comprising the steps of:
  (a) providing a recombinant poliovirus nucleic acid which lacks a nucleotide sequence encoding at least a portion of a capsid protein and a vaccinia virus-based expression vector the nucleic acid of which encodes at least a portion of a capsid protein and directs expression of at least a portion of a capsid protein; and
  (b) contacting a host cell with the recombinant poliovirus nucleic acid and the vaccinia virus-based expression vector under conditions appropriate for introduction of the recombinant poliovirus nucleic acid and the expression vector into the host cell; and
  (c) obtaining a yield of encapsidated viruses which substantially comprises encapsidated recombinant poliovirus nucleic acid.

51. An immunogenic composition comprising the encapsidated recombinant poliovirus nucleic acid of claim 38 and a physiologically acceptable carrier.

52. An immunogenic composition comprising the encapsidated recombinant poliovirus nucleic acid of claim 40 and a physiologically acceptable carrier.

53. An immunogenic composition comprising the encapsidated recombinant poliovirus nucleic acid of claim 43 and a physiologically acceptable carrier.

54. An immunogenic composition comprising the encapsidated recombinant poliovirus nucleic acid of claim 45 and a physiologically acceptable carrier.

55. An encapsidated recombinant poliovirus nucleic acid which lacks a nucleotide sequence such that the encapsidated recombinant poliovirus nucleic acid does not express proteins sufficient for encapsidation, the encapsidated recombinant poliovirus nucleic acid being substantially free of a nucleic acid which competes with the encapsidated recombinant poliovirus nucleic acid for proteins sufficient for encapsidation of the recombinant poliovirus nucleic acid.

56. The encapsidated recombinant poliovirus nucleic acid of claim 55, wherein the nucleotide sequence which the encapsidated recombinant poliovirus nucleic acid lacks is replaced by a foreign nucleotide sequence encoding, in an expressible a foreign protein or fragment thereof.

57. The encapsidated recombinant poliovirus nucleic acid of claim 56, wherein the foreign nucleotide sequence encodes a protein or fragment thereof selected from the group consisting of a viral antigen or fragment thereof, a bacterial antigen or fragment thereof, a tumor antigen or fragment thereof, an immunological response modifier or fragment thereof, and a protein with enzymatic activity or fragment thereof.

58. The encapsidated recombinant poliovirus nucleic acid of claim 57, wherein the viral antigen or fragment thereof is an HIV antigen or fragment thereof.

59. An immunogenic composition comprising the encapsidated recombinant poliovirus nucleic acid of claim 46 and a physiologically acceptable carrier.

60. An immunogenic composition comprising the recombinant poliovirus nucleic acid of claim 48 and a physiologically acceptable carrier.

61. An immunogenic composition comprising the recombinant poliovirus nucleic acid of claim 56 and a physiologically acceptable carrier.

62. An encapsidated recombinant poliovirus nucleic acid which does not express proteins sufficient for encapsidation, the encapsidated recombinant poliovirus nucleic acid being substantially free of nucleic acid which competes with the encapsidated recombinant poliovirus nucleic acid for proteins sufficient for encapsidation of the recombinant poliovirus nucleic acid.

63. An immunogenic composition comprising the recombinant poliovirus nucleic acid of claim 62 and a physiologically acceptable carrier.

64. An encapsidated recombinant poliovirus nucleic acid at least a portion of a capsid protein of which is encoded and expressed by an expression vector which lacks an infectious poliovirus genome, the encapsidated recombinant poliovirus nucleic acid further having a foreign nucleotide sequence substituted for a poliovirus nucleotide sequence which encodes at least a portion of a protein necessary for encapsidating the recombinant poliovirus nucleic acid, the foreign nucleotide sequence encoding, in an expressible form, a protein or fragment thereof.

* * * * *